United States Patent
Martich et al.

(10) Patent No.: US 11,839,678 B2
(45) Date of Patent: Dec. 12, 2023

(54) COMPOSITIONS, METHODS, AND KITS FOR ALTERING THE COLOR OF HAIR

(71) Applicant: L'Oreal, Paris (FR)

(72) Inventors: Jasmine Martich, Bronx, NY (US); Mohamed Amer Alkahwaji, Hoboken, NJ (US); Sarah Machover, New York, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 18/071,501

(22) Filed: Nov. 29, 2022

(65) Prior Publication Data

US 2023/0165770 A1    Jun. 1, 2023

Related U.S. Application Data

(60) Provisional application No. 63/284,588, filed on Nov. 30, 2021.

(30) Foreign Application Priority Data

Feb. 17, 2022    (FR) ..................... 22 01394

(51) Int. Cl.
*A61Q 5/10*    (2006.01)
*A61K 8/42*    (2006.01)
(Continued)

(52) U.S. Cl.
CPC .................. *A61K 8/42* (2013.01); *A61K 8/22* (2013.01); *A61K 8/342* (2013.01); *A61K 8/41* (2013.01); *A61K 8/92* (2013.01); *A61Q 5/065* (2013.01); *A61Q 5/08* (2013.01); *A61Q 5/10* (2013.01); *A61K 2800/48* (2013.01); *A61K 2800/51* (2013.01)

(58) Field of Classification Search
CPC . A61K 8/42; A61K 8/22; A61K 8/342; A61K 8/41; A61K 8/92; A61Q 5/065; A61Q 5/08; A61Q 5/10
USPC ............................................................ 8/405
See application file for complete search history.

(56) References Cited

U.S. PATENT DOCUMENTS

| | | |
|---|---|---|
| 4,003,699 A | 1/1977 | Rose et al. |
| RE30,199 E | 1/1980 | Rose et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

International Search Report and Written Opinion for counterpart Application No. PCT/US2022/051345, dated Mar. 24, 2023.

(Continued)

*Primary Examiner* — Eisa B Elhilo
(74) *Attorney, Agent, or Firm* — THE MARBURY LAW GROUP, PLLC

(57) ABSTRACT

The disclosure relates to hair color bases comprising (a) a surfactant system, (b) an alkaline component, (c) at least one chelating agent, (d) optionally, at least one natural oil, and (e) a solvent system, hair color altering compositions comprising the hair color bases, kits, and methods of altering the color of the hair.

24 Claims, 8 Drawing Sheets

1

2

3

4

(51) Int. Cl.
  *A61K 8/34* (2006.01)
  *A61K 8/92* (2006.01)
  *A61K 8/41* (2006.01)
  *A61Q 5/08* (2006.01)
  *A61Q 5/06* (2006.01)
  *A61K 8/22* (2006.01)

(56) References Cited

U.S. PATENT DOCUMENTS

| | | |
|---|---|---|
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 6,099,592 A | 8/2000 | Vidal et al. |
| 6,284,003 B1 | 9/2001 | Rose et al. |
| 6,730,789 B1 | 5/2004 | Birault et al. |
| 7,736,396 B2 | 6/2010 | Fukuhara et al. |
| 8,709,101 B2 | 4/2014 | Goget et al. |
| 2014/0230163 A1 | 8/2014 | Goget et al. |
| 2018/0177690 A1* | 6/2018 | Boulineau ............... A61K 8/817 |
| 2019/0191844 A1* | 6/2019 | Dreher .................. A61K 8/411 |
| 2019/0201309 A1* | 7/2019 | Machover .............. A61K 8/447 |
| 2021/0196606 A1 | 7/2021 | Shi et al. |

FOREIGN PATENT DOCUMENTS

| | | |
|---|---|---|
| DE | 4133957 A1 | 4/1993 |
| DE | 19543988 A1 | 5/1997 |
| EP | 0714954 A2 | 6/1996 |
| EP | 0770375 A1 | 5/1997 |
| FR | 2733749 A1 | 11/1996 |
| FR | 2801308 A1 | 5/2001 |
| FR | 2886136 A1 | 12/2006 |
| FR | 2968203 A1 | 6/2012 |
| FR | 2968208 A1 | 6/2012 |
| FR | 2980692 A1 | 4/2013 |
| FR | 2980696 A1 | 4/2013 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 2012/076535 A1 | 6/2012 |
| WO | 2012/076538 A1 | 6/2012 |
| WO | 2012/084509 A1 | 6/2012 |
| WO | 2013/045627 A1 | 4/2013 |
| WO | 2013/045628 A1 | 4/2013 |

OTHER PUBLICATIONS

French Search Report and Written Opinion for counterpart Application No. FR 2201394, dated Oct. 20, 2022.
Mintel: "Hair Colour," Modi-Mundipharma Beauty Products, Record No. 9060288, XP055973022, dated Oct. 25, 2021.
Mintel: "Permanent Root Colouring Kit," L'Oreal, Record No. 8292457, XP055973369, dated Nov. 25, 2020.

* cited by examiner

C8(20)  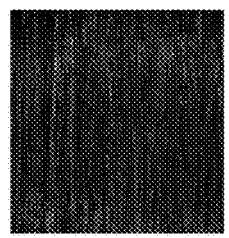          C7(20)  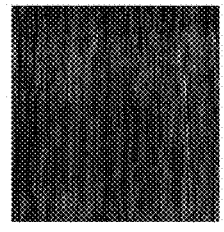
4C(20)  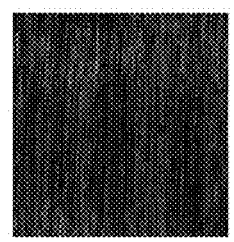          4E(20)  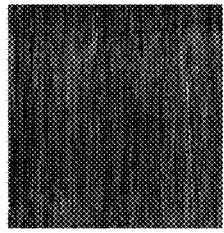
FIG. 2A                                FIG. 2B
C5(20)  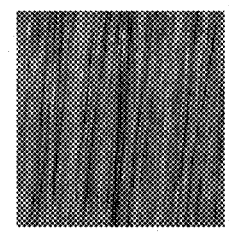          C6(20)  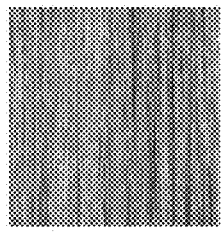
4F(20)  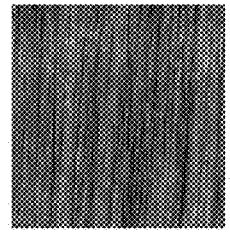          4D(20)  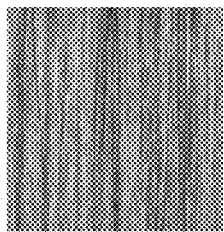
FIG. 2C                                FIG. 2D

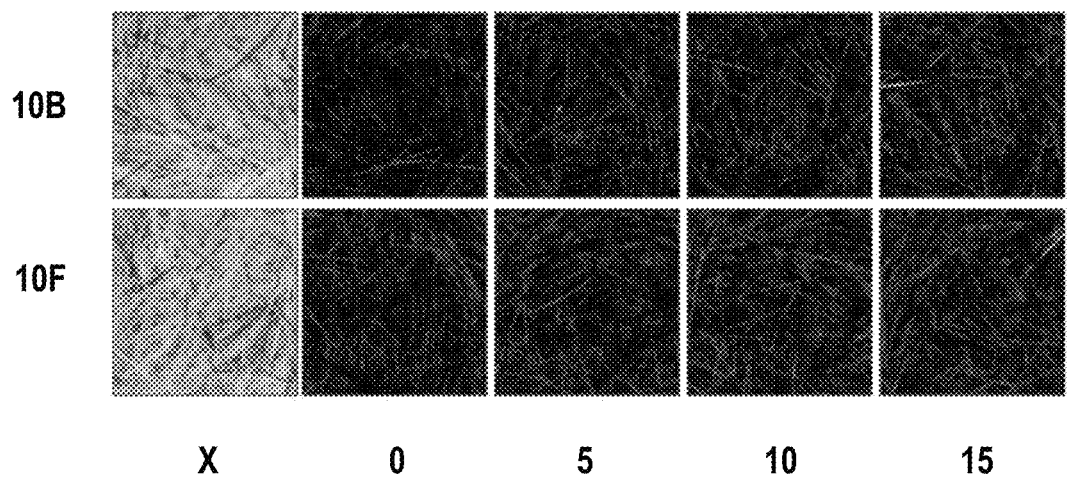
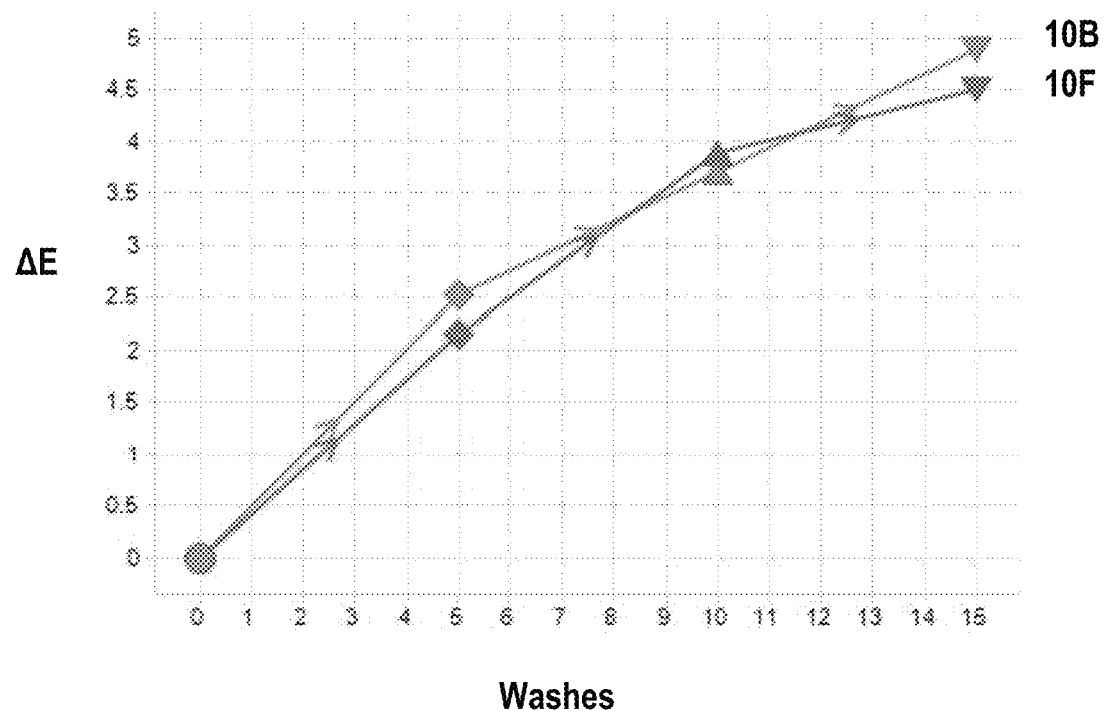
FIG. 4B

COMPOSITIONS, METHODS, AND KITS FOR ALTERING THE COLOR OF HAIR

CROSS REFERENCE TO RELATED APPLICATIONS

This application claims the benefit of priority to French Application No. FR 2201394, filed Feb. 17, 2022, and U.S. Provisional Application No. 63/284,588, filed Nov. 30, 2021, both of which are incorporated by reference herein in their entireties.

TECHNICAL FIELD

The present disclosure relates to hair color base compositions, hair color altering compositions comprising hair color bases, and kits and methods for altering the color of hair using the hair color bases and hair color altering compositions.

BACKGROUND

Changing or enhancing the appearance of hair is very popular with consumers, including for example changing hair color and/or imparting various properties, for example, shine and conditioning of the hair. Further, consumers often wish to deposit color onto hair in order to color or hide grey hair, e.g. on the head, facial hair, etc. Hair coloring typically involves bleaching, lightening, and/or changing the hair color through oxidative dyes, direct dyes, and/or pigments providing a different shade or color, and/or lifting the color of the hair.

Hair lightening processes, or lifting the color of hair, generally require the use of compositions that comprise at least one oxidizing agent to lighten the color of dark hair to lighter shades. When colorants or dye compounds such as oxidation dye precursors and/or direct dyes are present in these compositions, such compositions can change or deposit color while lightening the color of hair at the same time. Conventional hair coloring products are permanent dye compositions comprising oxidation dye precursors, which are also known as primary intermediates or couplers. These oxidation dye precursors are colorless or weakly colored compounds which, when combined with oxidizing agents, give rise to colored complexes by a process of oxidative condensation.

Variation in tone height before and after the application of a hair color-altering composition is typically evaluated when lightening or lifting the color of the hair. The degree or level of lightening or lift is determined by the variation. "Tone" refers to the "finish" of a shade, including is degree of warmth or coolness and is based on the classification of natural shades, one tone separating each shade from the shade immediately following or preceding it. Tone heights or levels typically range from 1 (black) to 10 (light blonde), one unit generally corresponding to one tone. Accordingly, the higher the tone number, the lighter the shade and the greater the degree of lift.

Hair dyeing or color lifting compositions may require one or more alkalizing agents, such as ammonia and/or ammonium-based compounds, which cause the hair shaft to swell, thus allowing small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. While such hair dyeing and/or color lifting compositions can effectively alter the color of hair, these compositions can damage the hair fibers and/or irritate the scalp due to excessively high levels of alkalinity.

Further, as consumers have become more aware of potential risks associated with using certain chemicals, the demand for cosmetic products, including hair coloring or hair dyeing compositions, which do not use certain ingredients, has increased.

Use of new and additional ingredients and novel combinations of ingredients are continuously sought in attempts to mitigate or avoid hair damage and/or scalp or skin irritation, as well as to provide hair color lifting and/or hair dyeing compositions that do not include, or minimize/limit the use of, mineral oil, certain alkalizing compounds such as ammonia and/or ammonium-based compounds, and/or certain dyes such as resorcinol and/or resorcinol derivatives, while achieving desired safety and performance objectives. However, the choice of ingredients or combinations of ingredients frequently poses difficulties insofar as they may be detrimental to the effectiveness of the composition in depositing color or lifting the color of the hair, or other cosmetic attributes. Ingredient combinations must be considered for attributes such as ease and uniformity of application, rheology or viscosity properties, stability of the compositions, color lastingness, and/or target shade formation, while weighing potential disadvantages such as increased damage and/or a less healthy look to the hair.

Thus, an objective of the present disclosure is to provide new compositions for altering the color of hair that provide consumers with desired properties such as ease and uniformity of application, rheology or viscosity properties, stability of the compositions, color lastingness, and/or target shade formation.

SUMMARY

The disclosure relates to hair color base compositions and hair color-altering compositions, as well as kits and methods for altering the color of hair.

In various embodiments, the disclosure relates to a hair color base comprising (a) a surfactant system, (b) at least one alkaline component, (c) at least one chelating agent, (d) optionally, at least one natural oil, and (e) a solvent system. Optionally, the hair color base may be free or substantially free of mineral oil, ammonia, ammonium hydroxide, and/or ammonium thiolactate.

In further embodiments, the disclosure relates to a hair color base comprising (a) a surfactant system comprising (i) at least one fatty amide, (ii) at least one alkoxylated fatty alcohol, (iii) at least one fatty alcohol other than the alkoxylated fatty alcohol, and, and (iv) at least one anionic surfactant, (b) at least one alkaline component, (c) at least one chelating agent, (d) optionally, at least one natural oil, and (e) a solvent system comprising (i) at least one glycol, (ii) at least one monoalcohol, and (iii) water. The hair color base may optionally comprise additional components, for example at least one thickening agent. Optionally, the hair color base may be free or substantially free of mineral oil, ammonia, ammonium hydroxide, and/or ammonium thiolactate.

In yet further embodiments, the disclosure relates to a hair color base comprising (a) from about 10% to about 40% of a surfactant system comprising (i) at least one fatty amide, (ii) at least one alkoxylated fatty alcohol, (iii) at least one fatty alcohol other than the alkoxylated fatty alcohol, and, and (iv) at least one anionic surfactant, (b) at least 5% of at least one organic alkalizing agent, (c) at least one chelating agent, (d) optionally, at least about 0.1% of at least one natural oil, and (e) a solvent system comprising (i) from about 3% to about 25% of at least one glycol, (ii) from about 3% to about 20% of at least one monoalcohol, and (iii) water, wherein all amounts are by weight, relative to the total weight of the hair color base. In various embodiments, the (b) at least one organic alkalizing agent may be chosen from monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures thereof. In various embodiments, the (c) at least one chelating agent may be chosen from chelating agents based on aminocarboxylic acids, iminodisuccinic acid, ethanoldiglycine acid, phosphonobutane tricarboxylic acid, tetrasodium glutamate diacetate, monophosphonic acid, polyphosphonic acid, polyphosphoric acid, or mixtures thereof. In various embodiments, the (e)(ii) at least one monoalcohol may be chosen from $C_1$-$C_{18}$ monoalcohols, such as $C_1$-$C_{16}$ monoalcohols, $C_2$-$C_{12}$ monoalcohols, or $C_2$-$C_8$ monoalcohols. The hair color base may optionally comprise additional components, for example at least one thickening agent. Optionally, the hair color base may be free or substantially free of mineral oil, ammonia, ammonium hydroxide, and/or ammonium thiolactate.

In still further embodiments, the disclosure relates to a hair color base comprising (a) from about 10% to about 40%, such as from about 12% to about 35%, from about 15% to about 30%, from about 17% to about 25%, or from about 18% to about 22%, of a surfactant system comprising (i) from about 2% to about 15%, such as from about 4% to about 12%, or from about 6% to about 10% of at least one fatty amide, (ii) from about 3% to about 15%, such as from about 4% to about 12%, from about 5% to about 10%, or from about 6% to about 8% of at least one alkoxylated fatty alcohol, (iii) from about 0.1% to about 5%, such as from about 0.25% to about 4%, from about 0.5% to about 3%, or from about 0.75% to about 2.5% of at least one fatty alcohol other than the alkoxylated fatty alcohol, and, and (iv) at least one anionic surfactant, (b) from about 5% to about 20%, such as from about 6% to about 18%, from about 7% to about 15%, or from about 8% to about 12% of at least one organic alkalizing agent, (c) from about 0.01% to about 2%, such as from about 0.05% to about 1%, from about 0.1% to about 0.8%, or from about 0.2% to about 0.5% of at least one chelating agent, (d) from about 0.1% to about 10%, such as from about 0.2% to about 8%, or from about 0.3% to about 6% of at least one natural oil, and (e) a solvent system comprising (i) from about 3% to about 25%, such as from about 3% to about 22%, from about 4% to about 20%, from about 5% to about 18%, or from about 6% to about 15% of at least one glycol, (ii) from about 3% to about 20%, such as from about 4% to about 18%, from about 5% to about 15%, from about 6% to about 12%, or from about 7% to about 10% of at least one monoalcohol, and (iii) water, wherein all amounts are by weight, relative to the total weight of the hair color base. In various embodiments, the (b) at least one organic alkalizing agent may be chosen from monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures thereof. In various embodiments, the (c) at least one chelating agent may be chosen from chelating agents based on aminocarboxylic acids, iminodisuccinic acid, ethanoldiglycine acid, phosphonobutane tricarboxylic acid, tetrasodium glutamate diacetate, monophosphonic acid, polyphosphonic acid, polyphosphoric acid, or mixtures thereof. In various embodiments, the (e)(ii) at least one monoalcohol may be chosen from $C_1$-$C_{18}$ monoalcohols, $C_1$-$C_{16}$ monoalcohols, $C_2$-$C_{12}$ monoalcohols, or $C_2$-$C_8$ monoalcohols. The hair color base may optionally comprise additional components, for example at least one thickening agent, for example in an amount ranging from about 0.1% to about 10%, such as from about 0.2% to about 8%, from about 0.3% to about 6%, or from about 0.5% to about 4%. Optionally, the hair color base may be free or substantially free of mineral oil, ammonia, ammonium hydroxide, and/or ammonium thiolactate.

In yet further embodiments, the disclosure relates to a hair color base comprising (a) from about 10% to about 40% of a surfactant system comprising (i) at least one fatty amide, (ii) at least one alkoxylated fatty alcohol, (iii) at least one fatty alcohol other than the alkoxylated fatty alcohol, and, and (iv) at least one anionic surfactant, (b) an alkaline component comprising (i) at least 0.5% of at least one organic alkalizing agent, and (ii) at least one mineral alkalizing agent, present in an amount up to about 15%, (c) at least one chelating agent, (d) optionally, at least about 0.1% of at least one natural oil, and (e) a solvent system comprising (i) from about 5% to about 30% of at least one glycol, (ii) from about 3% to about 20% of at least one monoalcohol, and (iii) water, wherein all amounts are by weight, relative to the total weight of the hair color base. In various embodiments, the (b) at least one organic alkalizing agent may be chosen from monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures thereof. In various embodiments, the (c) at least one chelating agent may be chosen from chelating agents based on aminocarboxylic acids, iminodisuccinic acid, ethanoldiglycine acid, phosphonobutane tricarboxylic acid, tetrasodium glutamate diacetate, monophosphonic acid, polyphosphonic acid, polyphosphoric acid, or mixtures thereof. In various embodiments, the (e)(ii) at least one monoalcohol may be chosen from $C_1$-$C_{18}$ monoalcohols, $C_1$-$C_{16}$ monoalcohols, $C_2$-$C_{12}$ monoalcohols, or $C_2$-$C_8$ monoalcohols. The hair color base may optionally comprise additional components, for example at least one thickening agent. Optionally, the hair color base may be free or substantially free of mineral oil, ammonia, ammonium hydroxide, and/or ammonium thiolactate.

In still further embodiments, the disclosure relates to a hair color base comprising (a) from about 10% to about 40%, such as from about 12% to about 40%, from about 15% to about 35%, from about 17% to about 33%, or from about 18% to about 30%, of a surfactant system comprising (i) from about 5% to about 25%, such as from about 6% to about 20%, from about 8% to about 18%, or from about 10% to about 16% of at least one fatty amide, (ii) from about 3% to about 20%, such as from about 4% to about 18%, from about 5% to about 15%, or from about 6% to about 12% of at least one alkoxylated fatty alcohol, (iii) from about 0.1% to about 6%, such as from about 0.25% to about 5%, from about 0.5% to about 4%, or from about 0.75% to about 3.5% of at least one fatty alcohol other than the alkoxylated fatty alcohol, and, and (iv) from about 0.5% to about 15%, such as from about 1% to about 10%, from about 2% to about 8%, or from about 3% to about 6% of at least one anionic surfactant, (b) an alkaline component comprising (i) at least 0.5%, such as from about 0.5% to about 10%, such as from about 1% to about 8%, from about 2% to about 7%, or from about 3% to about 6% of at least one organic alkalizing agent, and (ii) at least one mineral alkalizing agent, present in an amount up to about 15%, such as from about 0.01% to about 10%, such as from about 0.1% to about 8%, from about 0.2% to about 6%, or from about 0.3% to about 4%, (c) from about 0.01% to about 2%, such as from about 0.05% to about 1%, from about 0.1% to about 0.8%, or from about 0.2% to about 0.5% of at least one chelating agent, (d) from about 0.1% to about 10%, such as from about 0.2% to about 8%, or from about 0.3% to about 6% of at least one natural oil, and (e) a solvent system comprising (i) from about 6% to about 28%, such as from about 7% to about 25%, from about 8% to about 20%, or from about 9% to about 18% of at least one glycol, (ii) from about 4% to about 18%, such as from about 5% to about 15%, from about 6% to about 12%, or from about 7% to about 11% of at least one monoalcohol, and (iii) water, wherein all amounts are by weight, relative to the total weight of the hair color base. In various embodiments, the (b) at least one organic alkalizing agent may be chosen from monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures thereof. In various embodiments, the (c) at least one chelating agent may be chosen from chelating agents based on aminocarboxylic acids, iminodisuccinic acid, ethanoldiglycine acid, phosphonobutane tricarboxylic acid, tetrasodium glutamate diacetate, monophosphonic acid, polyphosphonic acid, polyphosphoric acid, or mixtures thereof. In various embodiments, the (e)(ii) at least one monoalcohol may be chosen from $C_1$-$C_{18}$ monoalcohols, $C_1$-$C_{16}$ monoalcohols, $C_2$-$C_{12}$ monoalcohols, or $C_2$-$C_8$ monoalcohols. The hair color base may optionally comprise additional components, for example at least one thickening agent, for example in an amount ranging from about 0.1% to about 10%, such as from about 0.2% to about 8%, from about 0.3% to about 6%, or from about 0.5% to about 4%. Optionally, the hair color base may be free or substantially free of mineral oil, ammonia, ammonium hydroxide, and/or ammonium thiolactate.

In one embodiment, the hair color base comprises (a) from about 15% to about 30% of a surfactant system comprising (i) at least one fatty amide, (ii) at least one alkoxylated fatty alcohol, (iii) at least one fatty alcohol other than the alkoxylated fatty alcohol, present in an amount up to about 3%, and (iv) at least one anionic surfactant; (b) an alkaline component comprising (i) at least about 0.5% of monoethanolamine, and (ii) at least one mineral alkalizing agent, present in an amount up to about 15%; (c) tetrasodium glutamate diacetate; (d) optionally, at least about 0.5% of at least one natural oil; and (e) a solvent system comprising (i) from about 10% to about 20% of at least one glycol, (ii) from about 5% to about 15% of at least one monoalcohol chosen from $C_2$-$C_{12}$ monoalcohols, and (iii) water, wherein all amounts are by weight, relative to the total weight of the hair color base. In a further embodiment, the hair color base comprises (a) from about 20% to about 30% of a surfactant system comprising (i) from about 8% to about 16% of at least one fatty amide, (ii) from about 5% to about 15% of at least one alkoxylated fatty alcohol, (iii) from about 0.5% to about 5% of at least one fatty alcohol other than the alkoxylated fatty alcohol, and (iv) from about 2% to about 8% of at least one anionic surfactant; (b) an alkaline component comprising (i) from about 2% to about 8% of monoethanolamine, and (ii) from about 0.5% to about 5% of at least one mineral alkalizing agent; (c) tetrasodium glutamate diacetate; (d) from about 0.5% to about 2% of at least one natural oil; and (e) a solvent system comprising (i) from about 5% to about 15% of at least one glycol, (ii) from about 5% to about 15% of at least one monoalcohol chosen from $C_2$-$C_8$ monoalcohols, and (iii) water, wherein the hair color base is free of mineral oil, ammonia, and/or ammonia hydroxide; and wherein all amounts are by weight, relative to the total weight of the hair color base.

The disclosure also relates to hair color compositions comprising a hair color base according to the disclosure and at least one hair color altering agent. The at least one hair color altering agent may be chosen from oxidation dyes, direct dyes, pigments, or mixtures thereof. The hair color altering compositions may, in some embodiments, be free or substantially free of para-phenylenediamines, resorcinol, and/or resorcinol derivatives. In some embodiments, the hair color altering compositions may be free or substantially free of one or more of mineral oil, ammonia, ammonium hydroxide, ammonium thiolactate, para-phenylenediamines, resorcinol, and/or resorcinol derivatives. In other embodiments, the hair color altering compositions may be free or substantially free of mineral oil, ammonia, ammonium hydroxide, ammonium thiolactate, para-phenylenediamines, resorcinol, and resorcinol derivatives.

The disclosure also relates to methods of altering the color of the hair. In various embodiments, the methods comprise mixing a hair color altering composition comprising a hair color altering base according to the disclosure with an oxidizing agent, or with a composition comprising an oxidizing agent, and applying the mixture to the hair. After an optional leave-on period ranging from about 1 to about 60 minutes, such as from about 5 to about 45 minutes, from about 10 to about 35 minutes, from about 15 to about 30 minutes, from about 20 to about 30 minutes, or from about 20 to about 25 minutes, the mixture may be rinsed from the hair.

The disclosure also relates to kits comprising (i) a first compartment containing a hair color base according to the disclosure, and optionally a hair color altering component, and (ii) a second compartment containing one or more compositions comprising an oxidizing agent; kits comprising (i) a first compartment containing a hair color base according to the disclosure, (ii) a second compartment containing a composition comprising an oxidizing agent, and (iii) a third compartment containing a hair color altering component; and/or kits comprising (i) a first compartment containing a hair color altering composition according to the disclosure, and (ii) a second compartment containing one or more compositions comprising an oxidizing agent.

BRIEF DESCRIPTION OF FIGURES

The accompanying figures, which are incorporated herein and constitute part of this specification, illustrate exemplary and non-limiting embodiments of the disclosure, and, together with the general description given above and the description provided herein, serve to explain various features of the disclosure.

FIG. 2A shows the color of identical hair swatches after treatment with comparative and inventive mixtures in Table 7.

FIG. 2B shows the color of identical hair swatches after treatment with comparative and inventive mixtures in Table 7.

FIG. 2C shows the color of identical hair swatches after treatment with comparative and inventive mixtures in Table 7.

FIG. 2D shows the color of identical hair swatches after treatment with comparative and inventive mixtures in Table 7.

FIGS. 4A-4D show results of a study to determine wash resistance of hair color altering compositions according to various embodiments of the disclosure, where X is the color of the hair swatch before treatment, 0 is the color of the hair swatch after initial treatment with the hair color altering composition followed by rinsing, shampooing, rinsing, and drying the swatch, and 5, 10, and 15 show the color of the hair swatches after 5, 10, and 15 subsequent washes, respectively. The change in color (ΔE) from 0 through 15 is also shown.

DETAILED DESCRIPTION

Figure 1A:
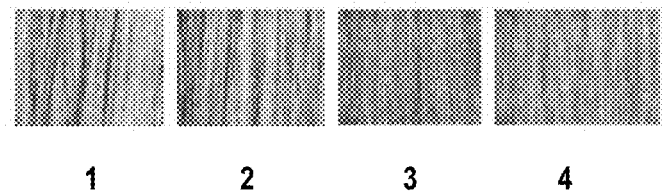
FIG. 1A shows the color of hair swatches 1-4 before treatment with the mixtures in Table 6.

It has been surprisingly and unexpectedly discovered that hair color altering compositions comprising hair color bases according to the disclosure are more stable than existing hair color altering compositions, are wash or fade resistant, and provide color deposition, lift, and/or target shade formation that is comparable to or even better than existing hair color altering compositions, even in the substantial absence of certain compounds traditionally used to impart such benefits. In addition, hair color bases according to the disclosure, and hair color altering compositions comprising hair color bases according to the disclosure, have been found to impart better properties to the hair during and after hair color altering processes than existing hair color altering compositions, such as, for example, easier to rinse the product from the hair, easier to comb/detangle when wet, and easier to blow dry, and once dry, the hair has more discipline, smoothness (both visual and tactile), and alignment, is more supple, and less dry. Further, hair color bases and hair color altering compositions according to the disclosure have viscosities that are particularly suited to efficient application to keratin fibers.

Thus, the present disclosure relates to hair color bases and to hair color altering compositions comprising the hair color bases. Kits, as well as methods of altering the color of the hair using the hair color bases and hair color altering compositions comprising hair color bases, are also disclosed.

Hair Color Bases

Hair color bases according to the disclosure can be used in compositions and methods for altering the color of the hair. The hair color bases comprise (a) a surfactant system, (b) an alkaline component, (c) at least one chelating agent, (d) optionally, at least one natural oil, and (e) a solvent system. In certain embodiments, the hair color base and/or hair color composition comprising the hair color base may be free or substantially free of ammonia or ammonium-based compounds, which includes but is not limited to ammonium hydroxide and ammonium thiolactate, may be free or substantially free of mineral oils, and/or may be free or substantially free of resorcinol and resorcinol derivatives.

Surfactant System

The hair color base according to the disclosure comprises a surfactant system. The surfactant system may be present in the hair color base in an amount ranging from about 10% to about 40% by weight, relative to the total weight of the hair color base. For example, the surfactant system may be present in the hair color base may be present in an amount ranging from about 12% to about 35%, such as from about 15% to about 30%, from about 17% to about 25%, or from about 18% to about 22% by weight, relative to the total weight of the hair color base. In further embodiments, the surfactant system may be present in the hair color base in an amount ranging from about 10% to about 35%, from about 10% to about 30%, from about 10% to about 25%, from about 10% to about 20%, from about 12% to about 40%, from about 12% to about 35%, from about 12% to about 30%, from about 12% to about 25%, from about 12% to about 20%, from about 15% to about 40%, from about 15% to about 35%, from about 15% to about 30%, from about 15% to about 25%, from about 15% to about 20%, from about 18% to about 40%, from about 18% to about 35%, from about 18% to about 30%, from about 18% to about 25%, or from about 18% to about 20% by weight, relative to the total weight of the hair color base.

The surfactant system present in the hair color base comprises a non-ionic component and an anionic component. The non-ionic component of the surfactant system includes (i) at least one fatty amide, (ii) at least one alkoxylated fatty alcohol, and (iii) at least one fatty alcohol other than the (ii) at least one alkoxylated fatty alcohol.

The term "fatty amide" as used herein means an amide comprising in its structure at least one hydrocarbon-based chain comprising at least 8 carbon atoms. For example, fatty amides useful herein may be compounds derived from an amide of alkanolamine and from a saturated or unsaturated, linear, or branched fatty acid comprising from 8 to 30 carbon atoms, the alkanolamine and/or the fatty acid optionally being oxyalkylenated, e.g. oxyethylenated, and comprising 1 to 50 mol of ethylene oxide. By way of example, fatty amides may include polyethoxylated fatty amides comprising from 2 to 30 mol of ethylene oxide.

In certain embodiments, oxyethylenated fatty amides may be chosen from compounds of the formula:

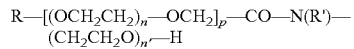

$R-[(OCH_2CH_2)_n-OCH_2]_p-CO-N(R')-(CH_2CH_2O)_{n'}-H$ wherein:

p denotes 0 or 1, n denotes a number ranging from 1 to 10, preferably from 1 to 6, n' denotes a number ranging from 1 to 100, preferably from 1 to 60, R' denotes a hydrogen atom or a $CH_2CH_2OH$ radical, preferably a hydrogen atom, and R denotes a $C_{10}$-$C_{30}$, preferably $C_{12}$-$C_{22}$, alkyl or alkenyl radical.

Examples of fatty amides which may be used include, but are not limited to, cocoamide DEA, cocoamide MEA, cocamide MIPA, cocamidopropylamine oxide, PEG-6 cocamide, trideceth-2 carboxamide MEA, PEG-4 rapeseedamide, or mixtures thereof. In some embodiments, the at least one fatty amide comprises PEG-4 rapeseedamide.

As a further example, polyglycerolated fatty amides may be chosen, for example those comprising from 1.5 to 5 glycerol groups, such as from 1.5 to 4 glycerol groups.

In certain embodiments, the at least one fatty amide may be present in the hair color base in an amount ranging from about 2% to about 15%, such as from about 4% to about 12%, or from about 6% to about 10% by weight, relative to the total weight of the hair color base.

As used herein, "alkoxylated fatty alcohol" refers to fatty alcohols with a carbon chain of C5 or greater, as defined above, further comprising at least one alkoxy group. For example, the at least one alkoxylated fatty alcohol may have a carbon chain of C8 or greater, C10 or greater, or C12 or greater. The at least one alkoxy group of the at least one alkoxylated fatty alcohol may, for example, be derived from an alkoxylation reaction carried out with an alkylene oxide. Non-limiting examples of at least one alkoxylated fatty alcohol include any fatty alcohol comprising at least one polyethylene glycol ether and any fatty alcohol comprising at least one polypropylene glycol ether.

In some embodiments, the alkoxylated fatty alcohol is chosen from ethoxylated fatty alcohols. For example, oxyethylenated fatty alcohols having an average degree of ethoxylation of less than 30, e.g. from 2 to 29, such as laureth-2, oleth-2, ceteareth-2, laneth-2, laureth-3, oleth-3, ceteareth-3, laureth-4, oleth-4, ceteareth-4, laneth-4, laureth-5, oleth-5, ceteareth-5, laneth-5, deceth-3, deceth-4, deceth-7, laureth-7, oleth-7, coceth-7, ceteth-7, ceteareth-7, C11-15 pareth-7, laureth-9, oleth-9, ceteareth-9, laureth-10, oleth-10, behenth-10, ceteareth-10, laureth-12, ceteareth-12, trideceth-12, ceteth-15, laneth-15, ceteareth-15, laneth-16, ceteth-16, oleth-16, steareth-16, oleth-20, ceteth-20, ceteareth-20, laneth-20, steareth-21, ceteareth-23, ceteareth-25, ceteareth-27, or mixtures of two or more of any of the foregoing, may be chosen. In some embodiments, the alkoxylated fatty alcohol comprises deceth-3, deceth-5, oleth-10, oleth-20, or mixtures thereof.

In certain embodiments, the at least one alkoxylated fatty alcohol may be present in the hair color base in an amount ranging from about 3% to about 15%, such as from about 4% to about 12%, from about 5% to about 10%, or from about 6% to about 8% by weight, relative to the total weight of the hair color base. For example, the at least one alkoxylated fatty alcohol may be present in the hair color base in an amount ranging from about 3% to about 12%, from about 3% to about 10%, from about 3% to about 8%, from about 4% to about 15%, from about 4% to about 10%, from about 4% to about 8%, from about 5% to about 15%, from about 5% to about 12%, from about 5% to about 8%, from about 6% to about 15%, from about 6% to about 12%, or from about 6% to about 10% by weight, relative to the total weight of the hair color base.

The hair color bases comprise at least one fatty alcohol other than the alkoxylated fatty alcohol. Non-limiting examples of fatty alcohols that may be chosen include saturated or unsaturated and linear or branched alcohols comprising from 6 to 40 carbon atoms, for example from 8 to 30 carbon atoms. In various embodiments, cetyl alcohol, isostearyl alcohol, stearyl alcohol and the mixture thereof (cetylstearyl alcohol/cetearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol, linoleyl alcohol, C9-11 alcohols, C10-16 alcohols, C12-13 alcohols, C12-15 alcohols, C14-15 alcohols, C14-22 alcohols, C20-22 alcohols, or mixtures of two or more of any of the foregoing, may be chosen. In some embodiments, the fatty alcohol other than the alkoxylated fatty alcohol comprises oleyl alcohol, octyldodecanol, C20-22 alcohols, or mixtures thereof. In further embodiments, the fatty alcohol other than the alkoxylated fatty alcohol comprises oleyl alcohol, octyldodecanol, or a mixture thereof. In one embodiment, the fatty alcohol other than the alkoxylated fatty alcohol comprises, consists essentially of, or consists of oleyl alcohol. In a further embodiment, the fatty alcohol other than the alkoxylated fatty alcohol comprises, consists essentially of, or consists of octyldodecanol.

As further examples, monoglycerolated or polyglycerolated fatty alcohols may also be chosen. For example, monoglycerolated or polyglycerolated C8-C40 alcohols may be chosen from compounds of the formula:

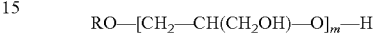

wherein R represents a linear or branched C8-C40, preferably C8-C30, alkyl or alkenyl radical, and m represents a number ranging from 1 to 30, preferably from 1 to 10.

For example, lauryl alcohol containing 4 mol of glycerol (INCI name: polyglyceryl-4 lauryl ether), lauryl alcohol containing 1.5 mol of glycerol, oleyl alcohol containing 4 mol of glycerol (INCI name: polyglyceryl-4 oleyl ether), oleyl alcohol containing 2 mol of glycerol (INCI name: polyglyceryl-2 oleyl ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol, or mixtures thereof, may be chosen.

In certain embodiments, the at least one fatty alcohol other than the alkoxylated fatty alcohol may be present in the hair color base in an amount ranging from about 0.1% to about 5%, such as from about 0.25% to about 4%, from about 0.5% to about 3%, or from about 0.75% to about 2.5% by weight, relative to the total weight of the hair color base. In certain embodiments, the total amount of the at least one fatty alcohol other than the alkoxylated fatty alcohol in the hair color base is no more than about 5%, such as no more than about 4%, or no more than about 3% by weight, relative to the total weight of the hair color base. In some embodiments, the at least one fatty alcohol other than the alkoxylated fatty alcohol may be present in the hair color base in an amount ranging from about 0.1% to about 4.5%, from about 0.1% to about 4%, from about 0.1% to about 3.5%, from about 0.1% to about 3%, from about 0.1% to about 2.5%, from about 0.1% to about 2%, from about 0.1% to about 1.5%, from about 0.25% to about 5%, from about 0.25% to about 4.5%, from about 0.25% to about 4%, from about 0.25% to about 3.5%, from about 0.25% to about 3%, from about 0.25% to about 2.5%, from about 0.25% to about 2%, from about 0.25% to about 1.5%, from about 0.5% to about 5%, from about 0.5% to about 4.5%, from about 0.5% to about 4%, from about 0.5% to about 3.5%, from about 0.5% to about 3%, from about 0.5% to about 2.5%, from about 0.5% to about 2%, from about 0.5% to about 1.5%, from about 0.75% to about 5%, from about 0.75% to about 4.5%, from about 0.75% to about 4%, from about 0.75% to about 3.5%, from about 0.75% to about 3%, from about 0.75% to about 2.5%, from about 0.75% to about 2%, or from about 0.75% to about 1.5% by weight, relative to the total weight of the hair color base.

The hair color base further comprises (iv) at least one anionic surfactant. Useful and non-limiting anionic surfactants include alkyl carboxylic acids, alkyl ether carboxylic acids, alkyl phosphates, alkyl ether phosphates, alkyl sulfates, alkyl ether sulfates, alkyl sulfonates, alkyl ether sulfonates, salts thereof, or mixtures thereof. In certain embodiments, the at least one anionic surfactant is chosen from alkyl ether carboxylic acids. For example, ceteareth-2 carboxylic acid, ceteareth-10 carboxylic acid, coceth-7 carboxylic acid, laureth-4 carboxylic acid, laureth-5 carboxylic acid, laureth-6 carboxylic acid, myreth-2 carboxylic acid, myreth-3 carboxylic acid, myreth-4 carboxylic acid, myreth-5 carboxylic acid, myreth-6 carboxylic acid, steareth-2 carboxylic acid, steareth-4 carboxylic acid, steareth-5 carboxylic acid, steareth-6 carboxylic acid, oleth-2 carboxylic acid, oleth-4 carboxylic acid, salts thereof, or mixtures of two or more of any of the foregoing, may be chosen. In some embodiments, the anionic surfactant comprises laureth-4 carboxylic acid, laureth-5 carboxylic acid, or a mixture thereof.

In certain embodiments, the at least one anionic surfactant may be present in the hair color base in an amount ranging from about 0.5% to about 15%, such as from about 1% to about 10%, from about 2% to about 8%, or from about 3% to about 6% by weight, relative to the total weight of the hair color base. For example, the at least one anionic surfactant may be present in the hair color base in an amount ranging from about 0.5% to about 12%, from about 0.5% to about 10%, from about 0.5% to about 8%, from about 0.5% to about 6%, from about 1% to about 15%, from about 1% to about 12%, from about 1% to about 8%, from about 1% to about 6%, from about 2% to about 15%, from about 2% to about 12%, from about 2% to about 10%, from about 2% to about 6%, from about 3% to about 15%, from about 3% to about 12%, from about 3% to about 10%, from about 3% to about 8% by weight, relative to the total weight of the hair color base.

Alkaline Component

Hair color bases according to the disclosure comprise an alkaline component. According to various embodiments, the alkaline component may comprise at least one organic alkalizing agent and/or at least one mineral alkalizing agent.

In certain embodiments, the alkaline component comprises at least one organic alkalizing agent chosen from monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris (hydroxymethyl)amino-methane, or mixtures thereof.

In further embodiments, the alkaline component comprises at least one mineral alkalizing agent chosen from ammonia, ammonium carbonates, sodium carbonates, potassium carbonates, ammonium bicarbonates, sodium bicarbonates, potassium bicarbonates, ammonium hydroxides, sodium hydroxides, potassium hydroxides, or mixtures thereof. In some embodiments, the alkaline component comprises ammonia and/or ammonium hydroxide.

In some embodiments, the alkaline component comprises at least one organic alkalizing agent and is free or substantially free of mineral alkalizing agents. For example, the alkaline component may comprise less than about 0.5%, less than about 0.4%, less than about 0.3%, less than about 0.2%, less than about 0.1%, or less than about 0.05% of mineral alkalizing agents. In certain embodiments, the alkaline component comprises at least one organic alkalizing agent and is free or substantially free of ammonia and/or ammonium-based compounds. In various embodiments, the alkaline component comprises monoethanolamine. In further embodiments, the alkaline component comprises monoethanolamine and is free or substantially free of ammonia and/or ammonium-based compounds.

In certain embodiments, the alkaline component comprises at least one organic alkalizing agent and is present in an amount of at least about 5% by weight, relative to the total weight of the hair color base. For example, the at least one organic alkalizing agent may be present in an amount ranging from about 5% to about 20%, such as from about 6% to about 18%, from about 7% to about 15%, or from about 8% to about 12% by weight, relative to the total weight of the hair color base. In further embodiments, the at least one organic alkalizing agent may be present in an amount ranging from about 5% to about 18%, from about 5% to about 15%, from about 5% to about 12%, from about 6% to about 20%, from about 6% to about 15%, from about 6% to about 12%, from about 7% to about 20%, from about 7% to about 18%, from about 7% to about 12%, from about 8% to about 20%, from about 8% to about 18%, or from about 8% to about 15% by weight, relative to the total weight of the hair color base.

In some embodiments, the alkaline component may comprise at least one organic alkalizing agent and be free or substantially free of mineral alkalizing agents, wherein the organic alkalizing agent is present in an amount of at least about 5% by weight, relative to the total weight of the hair color base. For example, the alkaline component may comprise at least one organic alkalizing agent and be free or substantially free of mineral alkalizing agents, wherein the organic alkalizing agent is present in an amount ranging from about 5% to about 20%, such as from about 6% to about 18%, from about 7% to about 15%, or from about 8% to about 12% by weight, relative to the total weight of the hair color base, such as from about 5% to about 18%, from about 5% to about 15%, from about 5% to about 12%, from about 6% to about 20%, from about 6% to about 15%, from about 6% to about 12%, from about 7% to about 20%, from about 7% to about 18%, from about 7% to about 12%, from about 8% to about 20%, from about 8% to about 18%, or from about 8% to about 15%.

In further embodiments, the alkaline component comprises at least one mineral alkalizing agent and is optionally free or substantially free of organic alkalizing agents. For example, in various embodiments the at least one mineral alkalizing agent may be present in an amount of at least 0.5% by weight, relative to the total weight of the hair color base, such as, for example, an amount ranging from about 1% to about 15%, such as from about 1.5% to about 12%, from about 2% to about 10%, from about 2.5% to about 8%, or from about 3% to about 6% by weight, relative to the total weight of the hair color base. In some embodiments, the alkaline component may comprise at least one mineral alkalizing agent, present in an amount ranging from about 0.01% to about 12%, such as from about 0.1% to about 11%, from about 0.5% to about 10%, or from about 1% to about 8% by weight, relative to the total weight of the hair color base. In some embodiments, the at least one mineral alkalizing agent is present in an amount ranging from about 0.1% to about 15%, from about 0.1% to about 13%, from about 0.1% to about 11%, from about 0.1% to about 10%, from about 0.1% to about 9%, from about 0.1% to about 8%, from about 0.1% to about 7%, from about 0.1% to about 6%, from about 0.1% to about 5%, from about 0.25% to about 15%, from about 0.25% to about 13%, from about 0.25% to about 11%, from about 0.25% to about 10%, from about 0.25% to about 9%, from about 0.25% to about 8%, from about 0.25% to about 7%, from about 0.25% to about 6%, from about 0.25% to about 5%, from about 0.5% to about 15%, from about 0.5% to about 13%, from about 0.5% to about 11%, from about 0.5% to about 10%, from about 0.5% to about 9%, from about 0.5% to about 8%, from about 0.5% to about 7%, from about 0.5% to about 6%, from about 0.5% to about 5%, from about 1% to about 15%, from about 1% to about 13%, from about 1% to about 11%, from about 1% to about 10%, from about 1% to about 9%, from about 1% to about 8%, from about 1% to about 7%, from about 1% to about 6%, or from about 1% to about 5% by weight, relative to the total weight of the hair color base.

In other embodiments, the alkaline component may comprise at least one organic alkalizing agent and at least one mineral alkalizing agent. For example, in various embodiments the at least one organic alkalizing agent may be present in an amount of at least 0.5% by weight, relative to the total weight of the hair color base, such as, for example, an amount ranging from about 1% to about 20%, such as from about 1.5% to about 18%, from about 2% to about 16%, from about 2.5% to about 14%, or from about 3% to about 12% by weight, relative to the total weight of the hair color base, and the at least one mineral alkalizing agent may be present in an amount of at least 0.001% by weight, relative to the total weight of the hair color base, such as, for example, an amount ranging from about 0.01% to about 10%, such as from about 0.05% to about 8%, from about 0.1% to about 7%, from about 0.2% to about 6%, or from about 0.3% to about 5% by weight, relative to the total weight of the hair color base. As further examples, in some embodiments, the alkaline component may comprise at least one organic alkalizing agent and at least one mineral alkalizing agent, wherein the at least one organic alkalizing agent is present in an amount of at least 0.5%, such as from about 0.5% to about 10%, such as from about 1% to about 8%, from about 2% to about 7%, or from about 3% to about 6% by weight, and the at least one mineral alkalizing agent is present in an amount ranging from about 0.001% to about 15%, such as from about 0.01% to about 10%, such as from about 0.1% to about 8%, from about 0.5% to about 5%, or from about 1% to about 3% by weight, relative to the total weight of the hair color base. In certain embodiments, the alkaline component comprises monoethanolamine in combination with ammonia and/or ammonium hydroxide.

In some non-limiting embodiments where the alkaline component comprises at least one organic alkalizing agent and at least one mineral alkalizing agent, the total amount of the alkaline component may range from about 1% to about 20%, such as from about 1.5% to about 18%, from about 2% to about 16%, from about 2.5% to about 15%, from about 3% to about 14%, or from about 4% to about 13% by weight, relative to the total weight of the hair color base, for example from about 1% to about 18%, from about 1% to about 16%, from about 1% to about 15%, from about 1% to about 14%, from about 1% to about 13%, from about 1% to about 12%, from about 1.5% to about 20%, from about 1.5% to about 16%, from about 1.5% to about 15%, from about 1.5% to about 14%, from about 1.5% to about 13%, from about 1.5% to about 12%, from about 2% to about 20%, from about 2% to about 18%, from about 2% to about 15%, from about 2% to about 14%, from about 2% to about 13%, from about 2% to about 12%, from about 2.5% to about 20%, from about 2.5% to about 18%, from about 2.5% to about 16%, from about 2.5% to about 14%, from about 2.5% to about 13%, from about 2.5% to about 12%, from about 3% to about 20%, from about 3% to about 18%, from about 3% to about 16%, from about 3% to about 15%, from about 3% to about 13%, from about 3% to about 12%, from about 4% to about 20%, from about 4% to about 18%, from about 4% to about 16%, from about 4% to about 15%, from about 4% to about 14%, or from about 4% to about 12% by weight, relative to the total weight of the hair color base.

Chelating Agent

Hair color bases according to the disclosure comprise at least one chelating agent. In some embodiments, the chelating agent may be chosen from organic acids and salts, thereof including carboxylic acids such as gluconic, citric, and tartaric acids. The salts of the organic acids of the present invention may contain an organic or inorganic cation. In some embodiments, the chelating agent is chosen from mono-, di-, or poly-, amino-, or hydroxy-carboxylic acids, mono-, di-, or poly-, amino-, or hydroxy-sulfonic acids, mono-, di-, or poly-, amino-, or hydroxy-phosphonic acids, or mixtures thereof.

In certain embodiments, useful chelating agents include those based on aminocarboxylic acids, iminodisuccinic acid, ethanoldiglycine acid, phosphonobutane tricarboxylic acid, tetrasodium glutamate diacetate, monophosphonic acid, polyphosphonic acid, polyphosphoric acid, or mixtures thereof. Non-limiting examples of useful chelating agents that may be chosen include ethylenediaminetetraacetic acid (EDTA), tripotassium phosphate, trisodium phosphate, disodium silicate, dipotassium silicate, sodium phytate, tetrasodium etidronate, tetrasodium pyrophosphate, pentasodium ethylenediamine tetramethylene phosphonate, sodium staminate, tetrasodium glutamate diacetate, or mixtures of two or more of any of the foregoing. In some embodiments, the chelating agent comprises EDTA, tetrasodium glutamate diacetate, or mixtures thereof. In some embodiments, the chelating agent comprises tetrasodium glutamate diacetate. In some embodiments, the chelating agent comprises tetrasodium glutamate diacetate and the hair color base is free or substantially free of other chelating agents.

According to various embodiments, the at least one chelating agent may be present in an amount ranging up to about 3%, such as from about 0.01% to about 2.5%, from about 0.05% to about 2%, from about 0.05% to about 1.5%, from about 0.1% to about 1%, or from about 0.1% to about 0.5% by weight, relative to the total weight of the hair color base. For example, the at least one chelating agent may be present in an amount ranging from about 0.01% to about 3%, from about 0.01% to about 2%, from about 0.01% to about 1.5%, from about 0.01% to about 1%, from about 0.01% to about 0.5%, from about 0.05% to about 3%, from about 0.05% to about 2.5%, from about 0.05% to about 1.5%, from about 0.05% to about 1%, from about 0.05% to about 0.5%, from about 0.1% to about 3%, from about 0.1% to about 2.5%, from about 0.1% to about 2%, or from about 0.1% to about 1.5% by weight, relative to the total weight of the hair color base.

Natural Oil

While not required, the hair color base according to the disclosure optionally comprises at least one natural oil. In various embodiments, the at least one natural oil is present in the hair color base in an amount of at least about 0.1% by weight, relative to the total weight of the hair color base. For example, in some embodiments the at least one natural oil may be present in an amount ranging from about 0.1% to about 8%, such as from about 0.1% to about 6%, from about 0.2% to about 5%, or from about 0.2% to about 2% by weight, relative to the total weight of the hair color base, such as, for example, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.2% to about 8%, from about 0.2% to about 7%, from about 0.2% to about 6%, from about 0.2% to about 4%, from about 0.2% to about 3%, from about 0.2% to about 1%, from about 0.3% to about 8%, from about 0.3% to about 7%, from about 0.3% to about 6%, from about 0.3% to about 5%, from about 0.3% to about 4%, from about 0.3% to about 3%, from about 0.3% to about 2%, from about 0.3% to about 1%, from about 0.4% to about 8%, from about 0.4% to about 7%, from about 0.4% to about 6%, from about 0.4% to about 5%, from about 0.4% to about 4%, from about 0.4% to about 3%, from about 0.4% to about 2%, or from about 0.4% to about 1% by weight, relative to the total weight of the hair color base.

By "natural oil," it is meant that the oil is derived from a plant, animal, or mineral. Non-limiting examples of oils derived from plants that can be used include olive oil, sweet almond oil, coconut oil, avocado oil, wheat germ oil, sunflower oil, grape seed oil, sesame oil, corn oil, apricot oil, castor oil, shea oil, soybean oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, camelina sativa seed oil, tamanu oil, babassu oil, pracaxi oil, and musk rose oil. A non-limiting example of oils of animal origin includes perhydrosqualene. As non-limiting examples of mineral oils, liquid paraffin and liquid petroleum jelly may be chosen.

Mixtures of two or more natural oils may also be chosen, such as, for example, mixtures of two or more oils of plant origin, two or more oils of animal origin, two or more oils of mineral origin, one or more oils of plant origin in combination with one or more oils of animal origin, one or more oils of plant origin in combination with one or more oils of mineral origin, one or more oils of animal origin in combination with one or more oils of mineral origin, two or more oils of plant origin in combination with one or more oils of animal origin, two or more oils of plant origin in combination with one or more oils of mineral origin, two or more oils of animal origin in combination with one or more oils of mineral origin, etc.

In one exemplary embodiment, the at least one natural comprises, consists essentially of, or consists of one or more plant oils. For example, the at least one natural oil may, in various embodiments, comprise at least one plant oil chosen from apricot oil, avocado oil, camelina sativa seed oil, jojoba oil, or mixtures thereof.

In some embodiments, the at least one natural oil comprises at least one plant oil, and the hair color base is free or substantially free of animal and/or mineral oils. In some embodiments, the hair color bases may comprise less than about 25%, such as less than about 20%, less than about 15%, or less than about 10% of animal and/or mineral oils, such as about 9% or less, about 8% or less, about 7% or less, about 6% or less, about 5% or less, about 4% or less, about 3% or less, about 2% or less, or about 1% or less. In various embodiments, the hair color bases comprise from about 0.001% to about 10% of animal and/or mineral oils, such as from about 0.01% to about 8%, or from about 0.1% to about 6% by weight, relative to the total weight of the composition. In another embodiment, the hair color base comprises no animal and/or mineral oils.

Solvent System

The hair color base according to the disclosure comprises a solvent system comprising at least one glycol, at least one monoalcohol, and water.

Useful and non-limiting glycols that may be used in the solvent system include ethylene glycol, diethylene glycol, triethylene glycol, tetraethylene glycol, pentaethylene glycol, propylene glycol, dipropylene glycol, tripropylene glycol, polyethylene glycol, caprylyl glycol, and hexylene glycol, as well as glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether. In certain embodiments, the at least one glycol may comprise hexylene glycol, propylene glycol, dipropylene glycol, or mixtures thereof.

According to various embodiments, the total amount of glycols in the hair color base ranges up to about 22%, such as from about 3% to about 22%, from about 4% to about 20%, from about 5% to about 18%, or from about 6% to about 15% by weight, relative to the total weight of the hair color base. For example, the total amount of glycols may range from about 1% to about 22%, from about 1% to about 20%, from about 1% to about 18%, from about 1% to about 16%, from about 1% to about 14%, from about 1% to about 12%, from about 1% to about 10%, from about 2% to about 22%, from about 2% to about 20%, from about 2% to about 18%, from about 2% to about 16%, from about 2% to about 14%, from about 2% to about 12%, from about 2% to about 10%, from about 3% to about 20%, from about 3% to about 18%, from about 3% to about 16%, from about 3% to about 14%, from about 3% to about 12%, from about 3% to about 10%, from about 4% to about 22%, from about 4% to about 18%, from about 4% to about 16%, from about 4% to about 14%, from about 4% to about 12%, from about 4% to about 10%, from about 5% to about 22%, from about 5% to about 20%, from about 5% to about 16%, from about 5% to about 14%, from about 5% to about 12%, from about 5% to about 10%, from about 6% to about 22%, from about 6% to about 20%, from about 6% to about 18%, from about 6% to about 16%, from about 6% to about 14%, from about 6% to about 12%, or from about 6% to about 10% by weight, relative to the total weight of the hair color base.

As used herein, the term "monoalcohols" means an alcohol having only one hydroxyl group. The monoalcohols may be linear, cyclic, or branched. For example, the at least one monoalcohol may be chosen from ethanol, propanol, isopropanol, butanol, pentanol, hexanol, heptanol, octanol, decanol, dodecanol, hexadecanol, octadecanol, eicosadecanol, 2-propanol, 2-methyl-1-propanol, 2-methyl-2-butanol, cetyl alcohol, stearyl alcohol, arachidyl alcohol, behenyl alcohol, cyclohexanol, or mixtures of any two or more of the foregoing.

In various embodiments, the monoalcohols that may be used in the solvent system of the hair color base include $C_1$-$C_{18}$ monoalcohols, such as, for example, $C_1$-$C_{16}$ monoalcohols, $C_2$-$C_{12}$ monoalcohols, or $C_2$-$C_8$ monoalcohols. In some embodiments, the monoalcohol is primary, meaning that the hydroxyl group is located on an end carbon.

In some embodiments, the monoalcohols that may be used in the solvent system of the hair color base are chosen from $C_2$-$C_8$ monoalcohols, such as, for example, ethanol, isopropanol, or mixtures thereof.

According to various embodiments, the total amount of monoalcohols in the hair color base ranges up to about 25%, such as from about 3% to about 25%, from about 4% to about 20%, from about 5% to about 18%, or from about 6% to about 15% by weight, relative to the total weight of the hair color base. For example, the total amount of monoalcohols in the hair color base may range from about 1% to about 25%, from about 1% to about 20%, from about 1% to about 18%, from about 1% to about 16%, from about 2% to about 25%, from about 2% to about 20%, from about 2% to about 18%, from about 2% to about 16%, from about 3% to about 20%, from about 3% to about 18%, from about 3% to about 16%, from about 4% to about 25%, from about 4% to about 18%, from about 4% to about 16%, from about 5% to about 25%, from about 5% to about 20%, from about 5% to about 16%, from about 6% to about 25%, from about 6% to about 20%, from about 6% to about 18%, or from about 6% to about 16% by weight, relative to the total weight of the hair color base.

The hair color base according to the disclosure comprises water. In various embodiments, the hair color base comprises water in a quantity sufficient ("QS") such that the amount of components other than water in combination with the total amount of water add up to 100%, when the amounts of all components are calculated by weight, relative to the total weight of the hair color base.

In various embodiments, the hair color base comprises water in an amount ranging up to about 60%, such as up to about 55%, up to about 50%, up to about 45%, up to about 40%, up to about 35%, up to about 30%, or up to about 25% by weight, relative to the total weight of the hair color base. In various embodiments, the hair color base comprises water in an amount greater than about 20%, such as, for example, greater than about 25%, or greater than about 30%. For example, the hair color base may comprise water in an amount ranging from about 20% to about 60%, from about 20% to about 55%, from about 25% to about 50%, from about 25% to about 45%, from about 25% to about 40%, from about 30% to about 45%, or from about 30% to about 40% by weight, relative to the total weight of the hair color base.

Thickening Agent

While not required, the hair color base optionally comprises at least one thickening agent. Useful and non-limiting thickening agents include polymeric thickeners and non-polymeric thickeners. The at least one polymeric thickener can be chosen from ionic or non-ionic, associative or non-associative polymers. Exemplary thickeners include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sodium carboxymethyl dextran, sodium carrageenan, tragacanth gum, xanthan gum, biosacharide gum, pullulan, hydroxypropylmethyl cellulose, hydroxyethyl cellulose, hydroxypropyl cellulose, polyvinyl pyrrolidone, carboxymethyl cellulose, polyacrylic acid, methylmethacrylate copolymer, carboxyvinyl polymer, dextrin, polyvinyl alcohol, carboxylated polyvinylalcohol, sulfonated polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, poloxamer polymers, or mixtures thereof.

In various embodiments, the at least one thickening agent is chosen from cellulose derivatives, acrylic acid and/or acrylate based polymers, poloxamer polymers, acacia, tragacanth, alginates, carrageenan, xanthan gum, petroleum jelly, waxes, starches, starch derivatives, clays colloidal silicon dioxide, microcrystalline cellulose, or mixtures thereof. In at least certain embodiments, the at least one thickening agent is chosen from polymeric thickening agents. By way of example, the at least one thickening agent may be chosen from poloxamer polymers. In some embodiments, the hair color base compositions comprise at least one thickening agent chosen from poloxamer polymers.

If present, the at least one thickening agent may be present in an amount ranging from about 0.1% to about 10%, such as from about 0.2% to about 8%, from about 0.3% to about 6%, or from about 0.5% to about 4% by weight, relative to the total weight of the hair color base. For example, the at least one thickening agent may be present in an amount ranging from about 0.1% to about 8%, about 0.1% to about 6%, about 0.1% to about 5%, about 0.1% to about 4%, about 0.1% to about 3%, about 0.1% to about 2%, about 0.2% to about 10%, about 0.2% to about 8%, about 0.2% to about 6%, about 0.2% to about 5%, about 0.2% to about 4%, about 0.2% to about 3%, about 0.2% to about 2%, about 0.3% to about 10%, about 0.3% to about 8%, about 0.3% to about 5%, about 0.3% to about 4%, about 0.3% to about 3%, about 0.3% to about 2%, about 0.4% to about 10%, about 0.4% to about 8%, about 0.4% to about 6%, about 0.4% to about 5%, about 0.4% to about 4%, about 0.4% to about 3%, about 0.4% to about 2%, about 0.5% to about 10%, about 0.5% to about 8%, about 0.5% to about 6%, about 0.5% to about 5%, about 0.5% to about 3%, or about 0.5% to about 2% by weight, relative to the total weight of the hair color base.

Additional Components

The hair color base may comprise additional components, such as, for example, pH adjusters; vitamins; amino acids, for example wheat amino acids; anionic, cationic, nonionic, amphoteric or zwitterionic polymers or mixtures thereof; antioxidants, for example erythorbic acid, sodium metabisulfite, and/or ammonium thiolactate; penetrants; fragrances; dispersants; film-forming agents; ceramides; preserving agents, for example phenoxyethanol; opacifiers; emulsifiers; conditioning agents; and/or auxiliary components. In at least certain embodiments, the composition is free or substantially free of ammonium thiolactate.

The additional components, individually or in total, may be present in an amount ranging from about 0.0001% to about 20%, such as from about 0.0001% to about 15%, from about 0.0001% to about 10%, from about 0.0001% to about 5%, from about 0.0001% to about 3%, from about 0.0001% to about 2%, or from about 0.0001% to about 1% by weight, relative to the total weight of the hair color base.

In certain embodiments, the hair color base is free or substantially free of mineral oil. In further embodiments, the hair color base is free or substantially free of ammonia and/or ammonium-based compounds. In yet further embodiments, the hair color base is free or substantially free of one or more of ammonia, ammonium-based compounds, and/or mineral oil. In still further embodiments, the hair color base is free or substantially free of ammonia, ammonium-based compounds, and mineral oil.

Viscosity

In various embodiments, the hair color base may have a viscosity that allows the composition to be applied to keratin fibers such as hair on the head, facial hair, etc., in a relatively convenient manner. For example, the composition may have a viscosity that provides a faster application time, less dripping or running, etc., compared to other hair color base compositions, and/or that allows the hair color base composition to be applied with an applicator designed for application of a composition with a particular viscosity.

By way of example only, the viscosity of the hair color base compositions may range from about 20 cps to about 150 cps, such as, for example, from about 20 to about 125 cps, about 20 to about 100 cps, about 20 to about 85 cps, about 20 to about 70 cps, about 25 to about 125 cps, about 25 to about 100 cps, about 25 to about 85 cps, about 25 to about 70 cps, about 30 to about 125 cps, about 30 to about 100 cps, about 30 to about 85 cps, about 30 to about 70 cps, about 50 to about 100 cps, about 60 to about 100 cps, about 70 to about 100 cps, about 50 to about 90 cps, about 50 to about 80 cps, or about 50 to about 75 cps, when measured at 25° C. using a #1 spindle at 100 rpm.

Hair Color Altering Composition

The disclosure also relates to compositions for altering the color of hair, comprising a hair color base according to the disclosure. The hair color base may comprise at least one hair color altering component, in which case the hair color base may be a hair color altering composition, or as an alternate embodiment, one or more hair color altering components may be present in a separate composition that is mixed with the hair color base to form a hair color altering composition before use. The hair color base and/or hair color altering composition may be mixed with a developer composition at or near the time of use to provide a mixture for altering the color of the hair.

Hair Color Altering Component

In various embodiments, the hair color base and/or hair color altering composition comprise at least one hair color altering component, which may be chosen from oxidation dyes, direct dyes, pigments, or mixtures thereof.

The oxidation dyes are generally chosen from one or more oxidation bases or precursors, optionally combined with one or more couplers. By way of example, the oxidation bases are chosen from para-phenylenediamines, bis(phenyl)alkylenediamines, para-aminophenols, ortho-aminophenols, meta-aminophenols, and heterocyclic bases, and the addition salts thereof.

Among the para-phenylenediamines that may be mentioned, for example, are para-phenylenediamine, para-toluenediamine (toluene-2,5-diamine), 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N, N-diethyl-para-phenylenediamine, N, N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, hydroxypropyl bis(n-hydroxyethyl-p-phenylenediamine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may be chosen.

Among the bis(phenyl)alkylenediamines that may be mentioned, for example, are N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof. Among the meta-aminophenols, 3-aminophenol and salts thereof, may be mentioned.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl) methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1, 5-a]pyridine, 3,4-diaminopyrazolo[1,5-a]pyridine, pyrazolo [1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-α-hydroxyethoxy-3-amino-pyrazolo[1,5-a]pyridine; 2-(4-diméthylpyperazinium-1-yl)-3-amino-pyrazolo[1,5-a] pyridine; hydroxyethoxy aminopryazolopyridine, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino methylpyrazole, and the addition salts thereof. 4,5-Diamino-1-(β-methoxyethyl)pyrazole may also be used. Optionally, a 4,5-diaminopyrazole may be used, for example 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, and 2,3-diamino-6-hydroxy-6,7-dihydro-1H,5H-pyrazolo[1,2-a]pyrazol-1-one. For example, 2,3-diamino-6,7-dihydro-1H,5H-pyrazolo[1,2-a]pyrazol-1-one and/or a salt thereof may be used.

According to some embodiments, 4,5-diamino-1-(β-hydroxyethyl)pyrazole and/or 2,3-diamino-6,7-dihydro-1H,5H-pyrazolo[1,2-a]pyrazol-1-one and/or a salt thereof may be used as heterocyclic bases.

Hair color altering compositions according to the disclosure may optionally comprise one or more couplers advantageously chosen from those conventionally used in the dyeing or coloring of hair. Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)benzene (2,4 diaminophenoxyethanol HCL), 2-amino-4-(β-hydroxyethylamino)-1-methoxy-benzene (2-methyl-5-hydroxyethylaminophenol), 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)-toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 4-amino-2-hydroxytoluene, 2-methylresorcinol, 4-chlororesorcinol, and 6-methylpyrazolo[1,5-a]benzimidazole, the addition salts thereof with an acid, or mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) may, for example, represent from about 0.0001% to about 15% by weight relative to the total weight of the composition, such as from about 0.0001% to about 12%, about 0.0001% to about 10%, about 0.0001% to about 8%, about 0.0001% to about 5%, about 0.001% to about 12%, about 0.001% to about 10%, about 0.001% to about 8%, about 0.001% to about 5%, about 0.005% to about 10%, about 0.005% to about 8%, about 0.005% to about 6%, or about 0.005% to 5% by weight, relative to the total weight of the composition.

The coupler(s), if they are present, may individually from about 0.0001% to about 15% by weight relative to the total weight of the composition, such as from about 0.0001% to about 12%, about 0.0001% to about 10%, about 0.0001% to about 8%, about 0.0001% to about 5%, about 0.001% to about 12%, about 0.001% to about 10%, about 0.001% to about 8%, about 0.001% to about 5%, about 0.005% to about 10%, about 0.005% to about 8%, about 0.005% to about 6%, or about 0.005% to 5% by weight, relative to the total weight of the composition.

Hair color altering compositions according to the invention may optionally comprise one or more synthetic or natural direct dyes, chosen from anionic and nonionic species, e.g. cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

In various embodiments, direct dyes are cationic direct dyes. Mention may be made of the hydrazono cationic dyes of formulas (Va) and (V'a), the azo cationic dyes (VIa) and (VI'a) and the diazo cationic dyes (VIIa) below:

Het⁺—C(Rᵃ)=N—N(Rᵇ)—Ar, An⁻ (Va)
Het⁺—N(Rᵃ)—N=C(Rᵇ)—Ar, An⁻ (V'a)
Het⁺—N=N—Ar, An⁻ (VIa)
Ar⁺—N=N—Ar″, An⁻ (VI'a) and
Het⁺—N=N—Ar'—N=N—Ar, An⁻ (VIIa)

in which formulas (Va), (V'a), (VIa), (VI'a) and (VIIa):

Het⁺ represents a cationic heteroaryl radical, optionally bearing an endocyclic cationic charge, such as imidazolium, indolium or pyridinium, optionally substituted preferentially with one or more $(C_1-C_8)$ alkyl groups such as methyl;

Ar⁺ representing an aryl radical, such as phenyl or naphthyl, bearing an exocyclic cationic charge, preferentially ammonium, particularly tri$(C_1-C_8)$alkylammonium such as trimethylammonium;

Ar represents an aryl group, especially phenyl, which is optionally substituted, preferentially with one or more electron-donating groups such as i) optionally substituted $(C_1-C_8)$alkyl, ii) optionally substituted $(C_1-C_8)$ alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1-C_8)$alkyl, hydroxyl or $(C_1-C_8)$alkoxy;

Ar″ is an optionally substituted (hetero)aryl group such as phenyl or pyrazolyl, which are optionally substituted, preferentially with one or more groups $(C_1-C_8)$alkyl, hydroxyl, (di)$(C_1-C_8)$(alkyl)amino, $(C_1-C_8)$alkoxy or phenyl;

Rᵃ and Rᵇ, which may be identical or different, represent a hydrogen atom or a group $(C_1-C_8)$alkyl, which is optionally substituted, preferentially with a hydroxyl group; or alternatively the substituent Rᵃ with a substituent of Het⁺ and/or Rᵇ with a substituent of Ar and/or Rᵃ with Rᵇ form, together with the atoms that bear them, a (hetero)cycloalkyl; particularly, Rᵃ and Rᵇ represent a hydrogen atom or a group $(C_1-C_4)$alkyl, which is optionally substituted with a hydroxyl group;

An⁻ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954.

In various embodiments, the cationic part is derived from the following:

(Va-1)

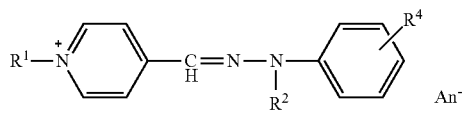

(VIa-1)

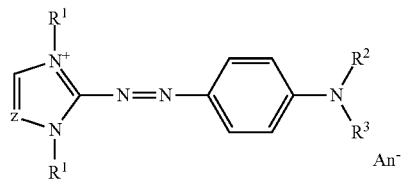

with:

R¹ representing a $(C_1-C_4)$ alkyl group such as methyl;

R² and R³, which are identical or different, represent a hydrogen atom or a $(C_1-C_4)$alkyl group, such as methyl; and R⁴ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group(s) with a hydroxyl group; particularly, R⁴ is a hydrogen atom, Z represents a CH group or a nitrogen atom, preferentially CH;

An⁻ represents an anionic counter-ion such as mesylate or halide.

In various embodiments, the dye of formulae (Va-1) and (VIa-1) is chosen from Basic Red 51, Basic Yellow 87, Basic Orange 31, or derivatives thereof:

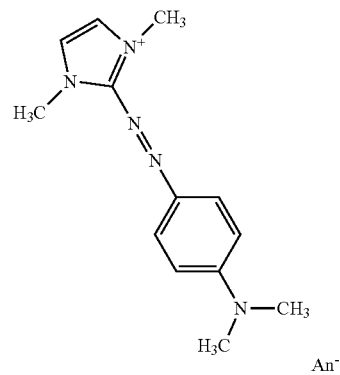

Basic Red 51

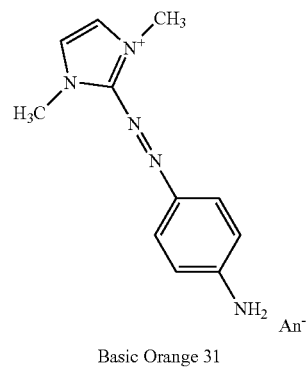

Basic Orange 31

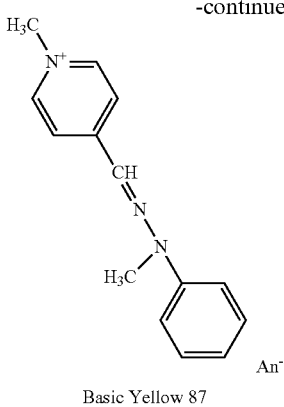

Basic Yellow 87

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When present, the direct dye(s) may, for example, be present in an amount ranging from 0.001% to 10% by weight, such as from 0.005% to 5% by weight, relative to the total weight of the composition.

Hair color altering compositions according to the disclosure may optionally comprise at least one pigment, alone or in combination with one or more oxidation dyes and/or direct dyes. These pigments may be in the form of powder or pigmentary paste, and may be coated or uncoated. The pigments may be chosen, for example, from mineral pigments, organic pigments, lakes, pigments with special effects such as nacres or glitter flakes, or mixtures thereof.

Exemplary and non-limiting mineral pigments include iron oxides, chromium oxides, manganese violet, ultramarine blue, chromium hydrate, ferric blue and titanium oxide.

Exemplary and non-limiting organic pigments include nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane and quinophthalone compounds. For example, the white or coloured organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470.

Composite pigments, which are pigment particles comprising a mineral core, at least one binder, and at least one organic pigment at least partially covering the core, may also be used.

Exemplary and non-limiting lakes include those which have dyes chosen from cochineal carmine, D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), and/or D&C Blue 1 (CI 42 090) adsorbed onto insoluble particles, e.g. inorganic substrates such as alumina, silica, calcium sodium borosilicate, calcium aluminium borosilicate, or aluminium. An example of a lake that may be used is D&C Red 7 (CI 15 850:1).

Useful pigments with special effects include any pigment that generally creates a non-uniform colored appearance (characterized by a certain shade, a certain vivacity, and/or a certain lightness) that changes as a function of the conditions of observation (e.g. light, temperature, observation angles, etc.). This may include, for example, pigments with a low refractive index, such as fluorescent, photochromic, or thermochromic pigments, and those with a higher refractive index, such as nacres or glitter flakes.

The size of the pigments is not limited, but may generally range from about 10 nm to about 200 nm, for example from about 20 nm to about 80 μm, or from about 30 nm to about 50 μm.

If present, the total amount of pigments may range from about 0.05% to about 20%, for example from about 0.1% to about 15% by weight, relative to the total weight of the composition.

The hair color altering compositions may optionally comprise any of the additional components described above for the hair color bases, but the skilled person will choose such components with care to maintain the desired pH of the hair color altering composition and/or the degree of lift imparted within an acceptable variation. Such additional components may be present in the hair color altering compositions as a component of the hair color altering composition, or may be present in the hair color altering compositions as a component of a hair color base that is added to the hair color altering composition.

The pH of the hair color altering composition may, in at least certain embodiments, be the same or substantially the same as the pH of the hair color base, for example prior to mixing the hair color base and oxidizing component. In some embodiments, the pH of the hair color altering composition may range from about 8 to about 12, such as, for example, from about 8 to about 11, from about 8.5 to about 10, or about 9.0 to about 9.5.

In certain embodiments, the hair color altering composition is free or substantially free of para-phenylenediamines. In further embodiments, the hair color altering composition is free or substantially free of resorcinol and/or resorcinol derivatives. In further embodiments, the hair color altering composition is free or substantially free of para-phenylenediamines, resorcinol, and resorcinol derivatives. In further embodiments, the hair color altering composition is free or substantially free of mineral oil. In still further embodiments, the hair color altering composition is free or substantially free of ammonia and/or ammonium-based compounds. In further embodiments, the hair color altering composition is free or substantially free of waxes. In yet further embodiments, the hair color altering composition is free or substantially free of one or more of para-phenylenediamines, resorcinol, resorcinol derivatives, ammonia, ammonium-based compounds, and/or mineral oil. In further embodiments still, the hair color altering composition is free or substantially free of para-phenylenediamines, resorcinol, resorcinol derivatives, ammonia, ammonium-based compounds, and mineral oil.

Viscosity

The viscosity of the hair color altering composition is typically the same as that described herein for the hair color base. For example, the viscosity of the hair color altering compositions may range from about 20 cps to about 150 cps, such as, for example, from about 20 to about 125 cps, about 20 to about 100 cps, about 20 to about 85 cps, about 20 to about 70 cps, about 25 to about 125 cps, about 25 to about 100 cps, about 25 to about 85 cps, about 25 to about 70 cps, about 30 to about 125 cps, about 30 to about 100 cps, about 30 to about 85 cps, about 30 to about 70 cps, about 50 to about 100 cps, about 60 to about 100 cps, about 70 to about 100 cps, about 50 to about 90 cps, about 50 to about 80 cps, or about 50 to about 75 cps, when measured at 25° C. using a #1 spindle at 100 rpm.

Developer Composition

The hair color altering compositions according to the disclosure may be mixed at or near the time of use with a developer composition (also referred to as an oxidizing composition) comprising at least one oxidizing agent.

The oxidizing agent may be, for example, chosen from peroxides, persulfates, perborates, percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be an oxidizing component.

In certain embodiments, the oxidizing agent is hydrogen peroxide. In various embodiments the hydrogen peroxide may be present in an aqueous solution whose titer may range from 1 to 40 volumes, such as from 5 to 40 volumes, from 5 to 30 volumes, or from 5 to 20 volumes. In certain embodiments, the oxidizing component is a 20V, 30V, or 40V hydrogen peroxide developer composition.

In other embodiments, the oxidizing agent is a persulfate and/or a monopersulfate such as, for example, potassium persulfate, sodium persulfate, ammonium persulfate, as well as mixtures thereof. In some embodiments, the oxidizing agents are chosen from hydrogen peroxide, potassium persulfate, sodium persulfate, or mixtures thereof.

The oxidizing agent may, in various embodiments, be present in the developer composition in an amount ranging from about 0.05% to about 50% by weight, such as from about 0.1% to about 30% by weight, from about 0.1% to about 20% by weight, about 1% to about 20%, about 1% to about 15%, about 1% to about 12%, about 3% to about 20%, about 3% to about 15%, about 3% to about 12%, about 5% to about 20%, about 5% to about 15%, about 5% to about 12%, about 7% to about 20%, about 7% to about 15%, about 7% to about 12%, about 9% to about 20%, about 9% to about 15%, or about 9% to about 12% by weight, based on the total weight of the developer composition.

The developer composition may contain at least one solvent, for example water, organic solvents, or mixtures thereof. Suitable organic solvents for use in the developer composition, alone or in mixture with water, include but are not limited to ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, or mixtures thereof.

The organic solvents for use according to the developer compositions can be volatile or non-volatile compounds. The organic solvent may, for example, be present in an amount ranging from about 0.5% to about 70% by weight, such as from about 2% to about 60% by weight, such as from about 5 to about 50% by weight, relative to the total weight of the developer composition.

The developer compositions may optionally include other components typically used in developer compositions, such as, for example, rheology-modifying agents, chelants, fatty substances, ceramides, pH adjusting agents, preservatives, fragrances, surfactants, etc.

The developer composition may be in the form of a powder, gel, liquid, foam, lotion, cream, mousse, or emulsion. In certain embodiments the developer composition is aqueous and is in the form of a liquid, cream, or emulsion. In other embodiments, the developer composition is anhydrous or substantially anhydrous.

In some non-limiting embodiments where the developer composition is liquid, e.g. aqueous, the developer composition may have a viscosity ranging from about 250 to about 2000 cps, such as, for example, from about 500 to about 2500 cps, about 500 to about 2000 cps, about 500 to about 1500 cps, about 600 to about 1300 cps, or about 650 to about 1200 cps when measured at 25° C. using a #4 spindle at 100 rpm.

Methods for Altering the Color of Hair

As described above, a hair color base may be mixed with a hair color altering agent and a developer composition, and/or a hair color altering composition may be mixed with a developer composition, e.g. at the time of or immediately before it is to be applied to the hair, such as up to about 30 minutes before, up to about 20 minutes before, or up to about 10 minutes before, for example about 1 to about 20 minutes before. The term "mixed" and all variations of this term as used herein refers to contacting or combining or reconstituting or dissolving or dispersing or blending or shaking the hair color base and/or hair color altering composition with the developer composition. It can also mean introducing the hair color base and/or hair color altering composition into the developer composition or vice versa. It may also mean placing the hair color base and/or hair color altering composition in the same vessel or container as the developer composition. A hair color altering component may optionally be present in the hair color base, hair color altering composition, developer composition, and/or a separate composition.

Thus, methods or processes for altering the color of keratin fibers, in particular human hair such as, for example, hair on the head (i.e. growing from the scalp), facial hair (e.g. beard or moustache hair), etc., in accordance with the disclosure comprise contacting a mixture comprising a hair color base or hair color altering composition and a developer composition with the keratin fibers such as hair. In various embodiments, keratin fibers do not include eyelashes, and the compositions according to the disclosure are not mascara compositions. As such, the compositions may be free or substantially free of waxes, or may comprise less than 3% wax, less than 2% wax, less than 1% wax, less than 0.5% wax, or less than 0.1% wax, relative to the total weight of the composition.

In some embodiments, a hair color base or hair color altering composition according to the disclosure can be mixed or combined with developer composition in a ratio by weight of from about 1:1 to about 1:10, such as from about 1:1 to about 1:4, such as from about 1:1 to about 1:3, or from about 1:1 to about 1:2, such as, for example about 1:1, about 1:2, about 1:3, or about 1:4. For example, a hair color base or hair color altering composition according to the disclosure can be mixed or combined with a 20V hydrogen peroxide developer composition in a ratio by weight of about 1:1.

When the hair color base or hair color altering composition according to the disclosure is mixed or combined with a developer composition, the viscosity of the mixture may, in some embodiments, permit the mixture to be applied to keratin fibers such as hair on the head, facial hair, etc., in a relatively convenient manner. For example, the mixture may have a viscosity that provides a faster application time, less dripping or running, etc., compared to other hair color mixtures, and/or that allows the mixture to be applied with an applicator designed for application of a composition with a particular viscosity.

By way of example only, the viscosity of the mixture may range from about 250 cps to about 2500 cps, such as, for example, from about 250 to about 2000 cps, about 250 to about 1800 cps, about 250 to about 1600 cps, about 300 to about 2000 cps, about 300 to about 1800 cps, about 300 to about 1600 cps, about 350 to about 2000 cps, about 350 to about 1800 cps, about 350 to about 1600 cps, about 400 to about 2000 cps, about 400 to about 1800 cps, about 400 to about 1600 cps, about 450 to about 2000 cps, about 450 to about 1800 cps, about 450 to about 1600 cps, about 500 to about 2000 cps, about 500 to about 1800 cps, or about 500 to about 1600 cps, when measured using a Rheomat RM 180, M3 spindle for 180 seconds under ambient conditions.

Upon application of the hair color altering composition, and after an optional resting time (leave-on or "processing" time) on the hair, for example, ranging from about 1 to about 60 minutes, such as from about 5 to about 45 minutes, from about 10 to about 35 minutes, from about 15 to about 30 minutes, or from about 20 to about 25 minutes, the hair is rinsed. The hair may further be optionally washed with shampoo, rinsed again, optionally washed with a hair conditioning composition, and/or rinsed again, then dried. The shampoo and hair conditioning composition can be any conventional hair shampoo and conditioner products.

The temperature that the process of altering the color of hair is carried out at is generally between room temperature and 80° C., for example between room temperature and 60° C.

According to various embodiments, the process and compositions may be used on hair that has not been previously artificially dyed or pigmented. In further embodiments, the process and composition disclosed herein may be also used on hair that has been previously artificially dyed or pigmented.

Various methods of altering the color of the hair according to the disclosure surprisingly and unexpectedly provide lastingness of color and/or target shade formation that is comparable to or even better than similar methods using existing hair color altering compositions, even in the substantial absence of certain compounds traditionally used to impart such benefits, such as, for example, para-phenylenediamines, resorcinol, and/or resorcinol derivatives. In addition, methods of altering the color of the hair according to the disclosure have been found to impart better properties to the hair during and after hair color altering processes than similar methods using existing hair color altering compositions. For example, it has been discovered that it is easier to rinse the product from the hair, and after rinsing the product from the hair, the hair is easier to comb/detangle when wet and easier to blow dry, and once dry, the hair has more discipline, smoothness (both visual and tactile), and alignment, is more supple, and less dry.

Kits

A further embodiment of the disclosure includes hair dye kits or multi-compartment devices comprising one or more separate compartments or containers.

For example, in one embodiment, a kit comprises (i) a first compartment containing a hair color base according to the disclosure, and optionally a hair color altering component, and (ii) a second compartment containing one or more developer compositions.

In a further embodiment, a kit comprises (i) a first compartment containing a hair color base according to the disclosure, (ii) a second compartment containing a developer composition, and (iii) a third compartment containing a hair color altering component.

In a still further embodiment, a kit comprises (i) a first compartment containing a hair color altering composition according to the disclosure, and (ii) a second compartment containing one or more developer compositions.

Other than in the examples, or where otherwise indicated, all numbers expressing quantities of components and/or reaction conditions are to be understood as being modified in all instances by the term "about" whether or not so stated, which encompasses ±10%, ±9%, ±8%, ±7%, ±6%, ±5%, ±4%, ±3%, ±2%, or ±1%. All numbers expressing quantities of components are given by weight, relative to the total weight of the composition in which the component is present, unless otherwise indicated.

"At least one" as used herein means one or more and thus includes individual components as well as mixtures/combinations. As used herein, when a composition is described as comprising an amount of "at least one" component, the recited amount is to be understood to include one or more than one such component, where the total amount of all such components are present in the amount described. For example, a composition comprising "from about 1% to about 20% of X" is understood to comprise one or more X, where the total amount of X ranges from about 1% to about 20%.

"Keratin fibers" include, but are not limited to, human hair. In one specific embodiment, the terms "keratin fibers," "hair," and the like exclude eyelashes.

The term "substantially anhydrous" as used herein means that the referenced composition is free or substantially free of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure. In some embodiments, the phrases "anhydrous or substantially anhydrous," or "free or substantially free of water," mean that the composition has no added water, but small or very small amounts of water may be present as a residual constituent of the various component(s) added to the compositions.

As used herein, a composition that is "free" of a component means that the component is not present in the composition as the individual component. For example, a composition may be "free" of wax meaning that no wax has been added into the composition, despite a pigment that is used in the composition being coated with a wax.

As used herein, a composition that is "substantially free" of a component means that the component is present in the composition in an amount less than 0.5%, less than 0.25%, less than 0.1%, less than 0.05%, less than 0.01%, less than 0.005%, or less than 0.001% by weight, relative to the total weight of the composition in which it is present.

All numbers expressing pH values are to be understood as being modified by the term "about," and as encompassing readings using a pH meter having a variation of up to ±10%, such as up to ±9%, up to ±8%, up to ±7%, up to ±6%, up to ±5%, up to ±4%, up to ±3%, up to ±2%, or up to ±1%, which a skilled person will recognize relates to the inherent variation in pH meters.

The term "altering the color" or "color-altering" as used herein may refer lifting or lightening the color of hair. It can also refer to dyeing or coloring hair or depositing color onto the hair. In certain instances, it refers to lifting or lightening the color of hair and depositing color onto the hair at the same time.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (a) and component (b). Furthermore, the phrase "formed from" does not limit the order of adding components to the composition or require that the listed components (e.g., components (a) and (b)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers as well as copolymers formed from at least two different types of monomers.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples that follow serve to illustrate embodiments of the present disclosure without, however, being limiting in nature.

EXAMPLES

Implementation of various embodiments of the present disclosure is demonstrated by way of the following non-limiting examples.

In the Examples below, all amounts are given by weight of active material, relative to the total weight of the composition in which they are present.

Example 1—Inventive Hair Color Bases

The inventive hair color base compositions in Tables 1A-1C were prepared, with varying alkaline components.

Example 1A—Organic Alkalizing Agents

The inventive hair color bases in Table 1A were prepared. The alkaline component in each of compositions 1A-1F was an organic alkalizing agent. The hair color base compositions were free of mineral alkalizing agents. Each of compositions 1A-1F was in the form of a liquid.

TABLE 1A

| | Inventive Hair Color Bases | | | | | |
|---|---|---|---|---|---|---|
| INCI | 1A | 1B | 1C | 1D | 1E | 1F |
| PEG-4 RAPESEEDAMIDE | 12.2 | 12.2 | 12.2 | 12.2 | 8.1 | 12.2 |
| ALKOXYLATED FATTY ALCOHOLS | 6.9 | 6.9 | 6.9 | 6.9 | 6.9 | 6.9 |
| OLEYL ALCOHOL | 1.1 | 1.1 | 1.1 | 1.1 | 1.1 | 1.1 |
| OCTYLDODECANOL | 1 | 1 | 1 | 1 | | |
| LAURETH-5 CARBOXYLIC ACID | 4.5 | 4.5 | 4.5 | 4.5 | 4.5 | 4.5 |
| POLYGLYCERYL-4 OLEYL ETHER | | | | | 5 | |
| ETHANOLAMINE | 9.8 | 9.8 | 9.8 | 9.8 | 11.2 | 9.8 |
| TETRASODIUM GLUTAMATE DIACETATE | 0.24 | 0.24 | 0.24 | 0.24 | 0.24 | 0.24 |
| *PRUNUS ARMENIACA* (APRICOT) KERNEL OIL | 2 | | | | | 2 |
| *CAMELINA SATIVA* SEED OIL | | 2 | | | | |
| *COCOS NUCIFERA* (COCONUT) OIL | | | 2 | | | |
| *PERSEA GRATISSIMA* (AVOCADO) OIL | | | | 2 | | |
| *SIMMONDSIA CHINENSIS* (JOJOBA) SEED OIL | | | | | 5 | |
| POLOXAMER 338 | 2 | 2 | 2 | 2 | 2 | 2 |
| GLYCOLS (hexylene, propylene, and/or dipropylene glycol) | 11.5 | 11.5 | 11.5 | 11.5 | 13.6 | 11.5 |
| ETHANOL (DENATURED) | 9.5 | 9.5 | 9.5 | 9.5 | 8.2 | 9.5 |
| ADDITIVES (fragrance, preservatives, antioxidants, amino acids) | <1 | <1 | <1 | <1 | <1 | <1 |
| WATER | QS | QS | QS | QS | QS | QS |

Example 1B—Organic Alkalizing Agents and Mineral Alkalizing Agents

The inventive hair color bases in Table 1B were prepared. The alkaline component in both of compositions 1G and 1H included both an organic alkalizing agent and a mineral alkalizing agent. Both of compositions 1G and 1H were in liquid form.

TABLE 1B

| INCI | Inventive Hair Color Bases | |
|---|---|---|
| | 1G | 1H |
| PEG-4 RAPESEEDAMIDE | 12.2 | 12.2 |
| ALKOXYLATED FATTY ALCOHOLS | 6.9 | 10.8 |
| OLEYL ALCOHOL | 3 | 1.1 |
| LAURETH-5 CARBOXYLIC ACID | 4.5 | 4.5 |
| AMMONIUM HYDROXIDE | 2 | 2 |
| ETHANOLAMINE | 4.5 | 4.5 |
| DISODIUM EDTA | 0.001 | 0.001 |
| TETRASODIUM GLUTAMATE DIACETATE | 0.24 | 0.24 |
| *PERSEA GRATISSIMA* (AVOCADO) OIL | 0.5 | 0.5 |
| POLOXAMER 338 | 2 | 2 |
| GLYCOLS (hexylene, propylene, and/or dipropylene glycol) | 11.5 | 11.5 |
| ETHANOL (DENATURED) | 9.5 | 9.5 |
| ADDITIVES (fragrance, preservatives, antioxidants, and/or amino acids) | <2 | <2 |
| WATER | QS | QS |

Example 1C—Mineral Alkalizing Agents

The inventive hair color base in Table 10 was prepared. The alkaline components in compositions 11 were mineral alkalizing agents. The hair color base composition was free of organic alkalizing agents.

TABLE 1C

| INCI | Inventive Hair Color Base 1I |
|---|---|
| PEG-4 RAPESEEDAMIDE | 12.2 |
| ALKOXYLATED FATTY ALCOHOLS | 6.9 |
| OLEYL ALCOHOL | 1.1 |
| LAURETH-5 CARBOXYLIC ACID | 4.5 |
| AMMONIUM HYDROXIDE | 4.5 |
| AMMONIUM THIOLACTATE | 0.5 |
| TETRASODIUM GLUTAMATE DIACETATE | 0.24 |
| POLOXAMER 338 | 2 |
| GLYCOLS (hexylene, propylene, and/or dipropylene glycol) | 11.5 |
| ETHANOL (DENATURED) | 8.2 |
| ADDITIVES (fragrance, preservatives, and/or antioxidants) | <2 |
| WATER | QS |

Example 2—Inventive Hair Color Bases

The inventive hair color base compositions in Tables 2A and 2B were prepared. Compositions 2A-2L included natural oils derived from plants, and were free of mineral oil. Each of compositions 2A-2M was in liquid form.

TABLE 2A

| INCI | Inventive Hair Color Bases | | | | | | |
|---|---|---|---|---|---|---|---|
| | 2A | 2B | 2C | 2D | 2E | 2F | 2G |
| PEG-4 RAPESEEDAMIDE | 8.13 | 8.13 | 8.13 | 8.13 | 8.13 | 8.13 | 8.13 |
| ALKOXYLATED FATTY ALCOHOLS | 6.9 | 6.9 | 6.9 | 6.9 | 6.9 | 6.9 | 6.9 |
| OLEYL ALCOHOL | 1.1 | 1.1 | 1.1 | 1.1 | 1.1 | 1.1 | 1.1 |
| LAURETH-5 CARBOXYLIC ACID | 4.5 | 4.5 | 4.5 | 4.5 | 4.5 | 4.5 | 4.5 |
| POLYGLYCERYL-4 OLEYL ETHER | 4.6 | 4.6 | 4.6 | 4.6 | 4.6 | 4.6 | 4.6 |
| ETHANOLAMINE | 9.8 | 9.8 | 11.2 | 11.2 | 11.2 | 11.2 | 11.2 |
| TETRASODIUM GLUTAMATE DIACETATE | 0.24 | 0.24 | 0.24 | 0.24 | 0.24 | 0.24 | 0.24 |
| *PRUNUS ARMENIACA* (APRICOT) KERNEL OIL | | | | | | 5 | |
| *CAMELINA SATIVA* SEED OIL | | 5 | | | | | 5 |
| *PERSEA GRATISSIMA* (AVOCADO) OIL | 5 | | 5 | 2.5 | | | |
| *SIMMONDSIA CHINENSIS* (JOJOBA) SEED OIL | | | | | | | 5 |
| POLOXAMER 338 | 2 | 2 | 2 | 2 | 2 | 2 | 2 |
| GLYCOLS (hexylene, propylene, and/or dipropylene glycol) | 13.6 | 13.6 | 7.6 | 7.6 | 13.6 | 13.6 | 13.6 |
| ETHANOL (DENATURED) | 9.5 | 9.5 | 8.2 | 8.2 | 8.2 | 8.2 | 8.2 |
| ADDITIVES (fragrance, preservatives, antioxidants, and/or amino acids) | <1 | <1 | <1 | <1 | <1 | <1 | <1 |
| WATER | QS | QS | QS | QS | QS | QS | QS |

TABLE 2B

| INCI | Inventive Hair Color Bases | | | | | |
|---|---|---|---|---|---|---|
| | 2H | 2I | 2J | 2K | 2L | 2M |
| PEG-4 RAPESEEDAMIDE | 8.13 | 8.13 | 8.13 | 8.13 | 8.13 | 8.13 |
| ALKOXYLATED FATTY ALCOHOLS | 6.9 | 6.9 | 6.9 | 6.9 | 10.4 | 6.9 |
| OLEYL ALCOHOL | 1.1 | 1.1 | 1.1 | 1.1 | 1.1 | 1.1 |
| LAURETH-5 CARBOXYLIC ACID | 4.5 | 4.5 | 6.8 | 4.5 | 4.5 | 4.5 |
| POLYGLYCERYL-4 OLEYL ETHER | 4.6 | 4.6 | | 7 | | 4.6 |
| ETHANOLAMINE | 11.2 | 11.2 | 11.2 | 11.2 | 11.2 | 11.2 |
| TETRASODIUM GLUTAMATE DIACETATE | 0.24 | 0.24 | 0.24 | 0.24 | 0.24 | 0.24 |
| *COCOS NUCIFERA* (COCONUT) OIL | 5 | | | | | |
| *PERSEA GRATISSIMA* (AVOCADO) OIL | | 5 | 0.5 | 0.5 | 0.5 | |
| MINERAL OIL | | | | | | 5 |
| POLOXAMER 338 | 2 | 2 | 2 | 2 | 2 | 2 |
| GLYCOLS (hexylene, propylene, and/or dipropylene glycol) | 13.6 | 13.6 | 12.2 | 12.2 | 12.2 | 13.6 |
| ETHANOL (DENATURED) | 8.2 | 8.2 | 8.2 | 8.2 | 8.2 | 8.2 |

TABLE 2B-continued

Inventive Hair Color Bases

| INCI | 2H | 2I | 2J | 2K | 2L | 2M |
|---|---|---|---|---|---|---|
| ADDITIVES (fragrance, preservatives, antioxidants, and/or amino acids) | <1 | <1 | <1 | <1 | <1 | <1 |
| WATER | QS | QS | QS | QS | QS | QS |

Example 3—Comparative Hair Color Bases

The comparative hair color base compositions in Table 3 were prepared. Both of compositions C1 and C2 were in liquid form.

TABLE 3

| INCI | Comparative Hair Color Bases | |
|---|---|---|
|  | C1 | C2 |
| PEG-4 RAPESEEDAMIDE | 8.13 | 11.62 |
| ALKOXYLATED FATTY ALCOHOLS | 6.9 | 9.9 |
| OLEYL ALCOHOL | 1.1 | 1.57 |
| LAURETH-5 CARBOXYLIC ACID | 4.5 | 6.43 |
| GLYCERYL LAURYL ETHER | 7 | 10 |
| POLYQUATERNIUM-6 | 1.4 | |
| AMMONIUM HYDROXIDE | 2.06 | |
| AMMONIUM THIOLACTATE | 0.47 | |
| ETHANOLAMINE | 4.5 | 5.2 |
| DISODIUM EDTA | 0.001 | |
| TETRASODIUM EDTA | 0.002 | |
| EDTA | 0.2 | 0.3 |
| *PERSEA GRATISSIMA* (AVOCADO) OIL | 0.5 | |
| POLOXAMER 338 | 2 | 2.86 |
| GLYCOLS (hexylene, propylene, and/or dipropylene glycol) | 12.2 | 17.5 |
| ETHANOL (DENATURED) | 8.2 | 11.7 |
| ADDITIVES (fragrance, preservatives, antioxidants, and/or amino acids) | <1 | <1 |
| WATER | QS | QS |

Two separate locks of hair were treated with either comparative hair color base composition C1 or inventive hair color base composition 1A (Table 1A). After the compositions were rinsed from the hair and while the hair was still wet, the lock of hair treated with inventive composition 1A was easier to comb and was easier to blow dry than the lock of hair treated with comparative composition C1. Once dry, the lock of hair treated with inventive composition 1A had better properties than the lock treated with comparative composition C1, for example less volume, less dryness, more discipline, more smoothness, and the individual hairs were more aligned.

Example 4—Inventive Hair Color Altering Compositions

The inventive hair color altering compositions in Tables 4A-4B were prepared.

Example 4A—Hair Color Compositions With Organic Alkalizing Agents

The inventive hair color altering compositions in Tables 4A were prepared with organic alkalizing agents. The hair color altering compositions were free of mineral alkalizing agents.

TABLE 4A

| | Inventive Hair Color Altering Compositions | | | | | |
|---|---|---|---|---|---|---|
| INCI | 4A | 4B | 4C | 4D | 4E | 4F |
| PEG-4 RAPESEEDAMIDE | 8.1 | 8.1 | 12.2 | 12.2 | 12.2 | 12.2 |
| ALKOXYLATED FATTY ALCOHOLS | 6.9 | 6.9 | 6.9 | 6.9 | 6.9 | 6.9 |
| OCTYLDODECANOL | | | 1.0 | 1.0 | 1.0 | 1.0 |
| OLEYL ALCOHOL | 1.1 | 1.1 | 1.1 | 1.1 | 1.1 | 1.1 |
| LAURETH-5 CARBOXYLIC ACID | 4.5 | 4.5 | 4.5 | 4.5 | 4.5 | 4.5 |
| POLYGLYCERYL-4 OLEYL ETHER | 4.6 | 4.6 | | | | |
| ETHANOLAMINE | 11.2 | 11.2 | 9.8 | 9.8 | 9.8 | 9.8 |
| TETRASODIUM GLUTAMATE DIACETATE | 0.2 | 0.2 | 0.2 | 0.2 | 0.2 | 0.2 |
| NATURAL OIL (avocado and/or coconut oil) | 0.5 | 2.5 | 2.0 | 2.0 | 2.0 | 2.0 |
| POLOXAMER 338 | 2.0 | 2.0 | 2.0 | 2.0 | 2.0 | 2.0 |
| GLYCOLS (hexylene, propylene, and/or dipropylene glycol) | 13.6 | 13.6 | 11.5 | 11.5 | 11.5 | 11.5 |
| ETHANOL (DENATURED) | 8.2 | 8.2 | 9.5 | 9.5 | 9.5 | 9.5 |
| HAIR COLOR ALTERING AGENTS* | | | 3.56 | 0.52 | 4.28 | 1.18 |
| ADDITIVES (fragrance, antioxidants) | <1 | <1 | <1 | <1 | <1 | <1 |
| WATER | QS to 100 | QS to 100 | QS to 100 | QS to 100 | QS to 100 | QS to 100 |

*Hair color altering compositions in Table 4A included resorcinol, 2-methylresorcinol, 2,4-diaminophenoxyethanol HCl, toluene-2,5-diamine, and m-aminophenol.

Example 4B—Hair Color Compositions with Organic and Mineral Alkalizing Agents The inventive hair color altering compositions in Table 4B were prepared with organic and mineral alkalizing agents.

TABLE 4B

| | Inventive Hair Color Altering Compositions | | | | | |
|---|---|---|---|---|---|---|
| INCI | 4G | 4H | 4I | 4J | 4K | 4L |
| PEG-4 RAPESEEDAMIDE | 8.1 | 8.1 | 8.1 | 12.2 | 12.2 | 12.2 |
| ALKOXYLATED FATTY ALCOHOLS | 6.9 | 6.9 | 6.9 | 10.8 | 10.8 | 10.8 |
| OLEYL ALCOHOL | 1.1 | 1.1 | 1.1 | 1.1 | 1.1 | 1.1 |
| LAURETH-5 CARBOXYLIC ACID | 4.5 | 4.5 | 4.5 | 4.5 | 4.5 | 4.5 |
| GLYCERYL LAURYL ETHER | 7.0 | 7.0 | 7.0 | | | |
| AMMONIUM HYDROXIDE | | | | 2.1 | 1.6 | 1.6 |
| AMMONIUM THIOLACTATE | 0.46 | 0.46 | 0.46 | | | |
| ETHANOLAMINE | 10.9 | 8.2 | 8.2 | 4.5 | 4.5 | 4.5 |
| TETRASODIUM GLUTAMATE DIACETATE | 0.24 | 0.24 | 0.24 | 0.24 | 0.24 | 0.24 |
| *PERSEA GRATISSIMA* (AVOCADO) OIL | 0.5 | 0.5 | 0.5 | 0.5 | 0.5 | 0.5 |
| POLOXAMER 338 | 2.0 | 2.0 | 2.0 | 4.0 | 4.0 | 4.0 |
| GLYCOLS (hexylene, propylene, and/or dipropylene glycol) | 12.2 | 12.2 | 12.2 | 11.5 | 11.5 | 11.5 |
| ETHANOL (DENATURED) | 8.2 | 8.2 | 8.2 | 9.5 | 9.5 | 9.5 |

TABLE 4B-continued

| | Inventive Hair Color Altering Compositions | | | | | |
|---|---|---|---|---|---|---|
| INCI | 4G | 4H | 4I | 4J | 4K | 4L |
| HAIR COLOR ALTERING AGENTS* | | 0.52 | 0.70 | | | |
| ADDITIVES (fragrance, antioxidants) | <1 | <1 | <1 | <2 | <2 | <2 |
| WATER | QS to 100 | QS to 100 | QS to 100 | QS to 100 | QS to 100 | QS to 100 |

*Hair color altering compositions in Table 4B included resorcinol, 2-methylresorcinol, 2,4-diaminophenoxyethanol HCl, toluene-2,5-diamine, thioglycerin, m-aminophenol, and/or p-aminophenol.

Example 5—Comparative Hair Color Altering Compositions

The comparative hair color altering compositions in Table 5 were prepared.

TABLE 5

| | Comparative Hair Color Altering Compositions | | | | | |
|---|---|---|---|---|---|---|
| INCI | C3 | C4 | C5 | C6 | C7 | C8 |
| C20-22 ALCOHOLS | 4.6 | 4.6 | 4.6 | 4.6 | 4.6 | 4.6 |
| CETYL HYDROXY-ETHYLCELLULOSE | 0.05 | 0.05 | 0.05 | 0.05 | 0.05 | 0.05 |
| EDTA | 0.2 | 0.2 | 0.2 | 0.2 | 0.2 | 0.2 |
| CETYL PALMITATE | 2.0 | 2.0 | 2.0 | 2.0 | 2.0 | 2.0 |
| ETHANOLAMINE | 4.4 | 4.4 | 4.4 | 4.4 | 4.4 | 4.4 |
| MINERAL OIL | 60.0 | 60.0 | 60.0 | 60.0 | 60.0 | 60.0 |
| ALKOXYLATED FATTY ALCOHOLS | 6.1 | 6.1 | 6.1 | 6.1 | 6.1 | 6.1 |
| 2-OLEAMIDO-1,3-OCTADECANEDIOL | 0.01 | 0.01 | 0.01 | 0.01 | 0.01 | 0.01 |
| HAIR COLOR ALTERING AGENTS* | | 0.44 | 0.52 | 0.33 | 0.83 | 1.40 |
| ADDITIVES (amino acids, vitamins, antioxidants, fragrance, extracts) | <1 | <1 | <1 | <1 | <1 | <1 |
| WATER | QS to 100 | QS to 100 | QS to 100 | QS to 100 | QS to 100 | QS to 100 |

*Hair color altering compositions in Table 5 included resorcinol, 2-methylresorcinol, 2,4-diaminophenoxyethanol HCl, toluene-2,5-diamine, thioglycerin, m-aminophenol, p-aminophenol, and/or hydroxybenzomorpholine.

Example 6—Evaluation of Color Deposit and Coverage

Inventive and comparative hair color altering compositions were mixed with equal amounts of aqueous hydrogen peroxide oxidizing compositions (20V or 30V), as shown in Table 6.

TABLE 6

| Mixture | Hair Color Altering Composition | Oxidizing Composition | Mixing Ratio | Leave-On Time (minutes) |
|---|---|---|---|---|
| 4H$_{(20)}$ | 4H | 20V | 1:1 | 30 |
| 4H$_{(30)}$ | 4H | 30V | 1:1 | 30 |
| 4I$_{(20)}$ | 4I | 20V | 1:1 | 30 |
| 4I$_{(30)}$ | 4I | 30V | 1:1 | 30 |
| C4$_{(20)}$ | C4 | 20V | 1:1 | 35 |

Once the mixtures in Table 6 were prepared, each mixture was applied to four different swatches of dark blonde hair at a rate of 3 grams of mixture to 1 gram of hair, to determine the efficacy of color deposit and coverage for each mixture. After a leave-on time, the swatches were rinsed, shampooed, rinsed again, and dried. Once dry, the swatches were evaluated for color deposit and coverage.

Figure 1B:
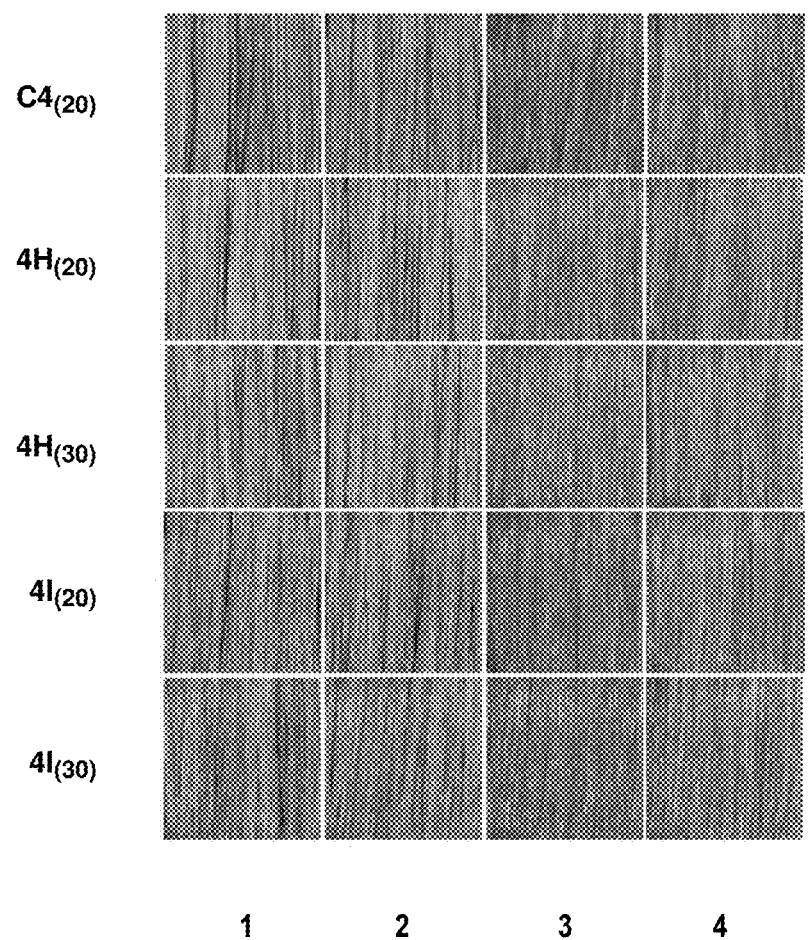
FIG. 1B shows the color of hair swatches 1-4 after treatment with the mixtures in Table 6.

As can be seen in FIGS. 1A and 1B, the color deposit and coverage provided by each of the inventive mixtures was comparable to that seen by the comparative mixture, despite the comparative mixture having a large amount of mineral oil and a different solvent system than the inventive mixtures.

This example demonstrates that, surprisingly and unexpectedly, satisfactory color deposit and coverage can be achieved that is comparable to traditional hair color altering compositions.

Example 7—Evaluation of Shade Matching

Inventive and comparative hair color altering compositions were mixed with equal amounts of 20V aqueous hydrogen peroxide oxidizing compositions, as shown in Table 7.

TABLE 7

| Mixture | Hair Color Altering Composition | Oxidizing Composition | Mixing Ratio |
|---|---|---|---|
| 4C$_{(20)}$ | 4C | 20V | 1:1 |
| 4D$_{(20)}$ | 4D | 20V | 1:1 |
| 4E$_{(20)}$ | 4E | 20V | 1:1 |
| 4F$_{(20)}$ | 4F | 20V | 1:1 |
| C5$_{(20)}$ | C5 | 20V | 1:1 |
| C6$_{(20)}$ | C6 | 20V | 1:1 |
| C7$_{(20)}$ | C7 | 20V | 1:1 |
| C8$_{(20)}$ | C8 | 20V | 1:1 |

Once the mixtures in Table 7 were prepared, each mixture was applied to swatches of hair at a rate of 3 grams of mixture to 1 gram of hair, to ascertain the ability of each of the inventive compositions to match the shade of each of the comparative compositions. After a leave-on time, the swatches were rinsed, shampooed, rinsed again, and dried. Once dry, the swatches were evaluated.

As can be seen in FIGS. 2A-2D, the shade obtained by each of the inventive mixtures was comparable to that of the respective comparative mixtures, despite the comparative mixtures having a large amount of mineral oil, a lower amount of organic oxidizing agent, and a different solvent system than the inventive mixtures.

This example demonstrates that, surprisingly and unexpectedly, hair color altering compositions according to the disclosure are able to satisfactorily match the shades achieved by traditional hair color altering compositions.

Example 8—Evaluation of Lift

Inventive and comparative hair color bases and hair color altering compositions were mixed with equal amounts of 20V aqueous hydrogen peroxide oxidizing compositions, as shown in Table 8.

TABLE 8

| Mixture | Hair Color Base/ Hair Color Altering Composition | Oxidizing Composition | Mixing Ratio |
|---|---|---|---|
| 2E$_{(20)}$ | 2E | 20V | 1:1 |
| 2F$_{(20)}$ | 2F | 20V | 1:1 |

TABLE 8-continued

| Mixture | Hair Color Base/ Hair Color Altering Composition | Oxidizing Composition | Mixing Ratio |
|---|---|---|---|
| 2M(20) | 2M | 20V | 1:1 |
| 4A(20) | 4A | 20V | 1:1 |
| 4B(20) | 4B | 20V | 1:1 |
| 4G(20) | 4G | 20V | 1:1 |
| C1(20) | C1 | 20V | 1:1 |
| C3(20) | C3 | 20V | 1:1 |

Once the mixtures in Table 8 were prepared, each mixture was applied to three (3) different swatches of hair (dark brown, dark blonde, light blonde) at a rate of 3 grams of mixture to 1 gram of hair, to ascertain the ability of each of the inventive compositions to lift the color of the hair compared to the comparative compositions. After a leave-on time, the swatches were rinsed, shampooed, rinsed again, and dried. Once dry, the swatches were evaluated.

Figure 3A:
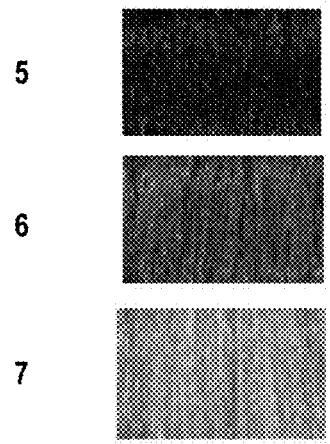
FIG. 3A shows the color of hair swatches 5-7 before treatment with the mixtures in Table 8.
Figure 3B:
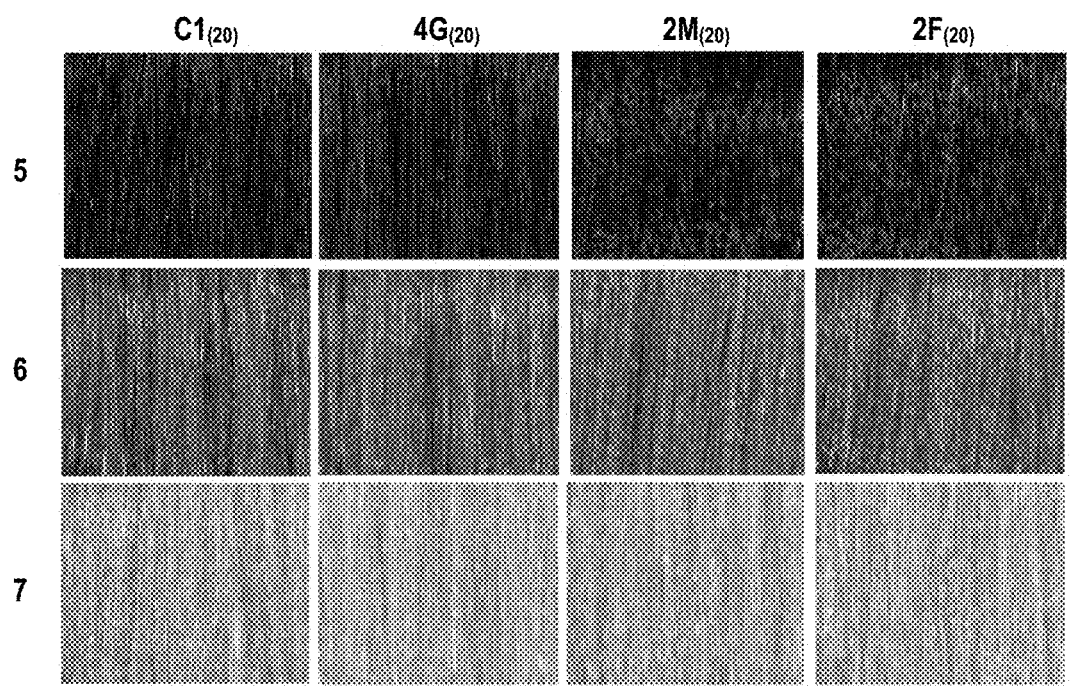
FIG. 3B shows the color of hair swatches 5-7 after treatment with mixtures in Table 8.
Figure 3C:
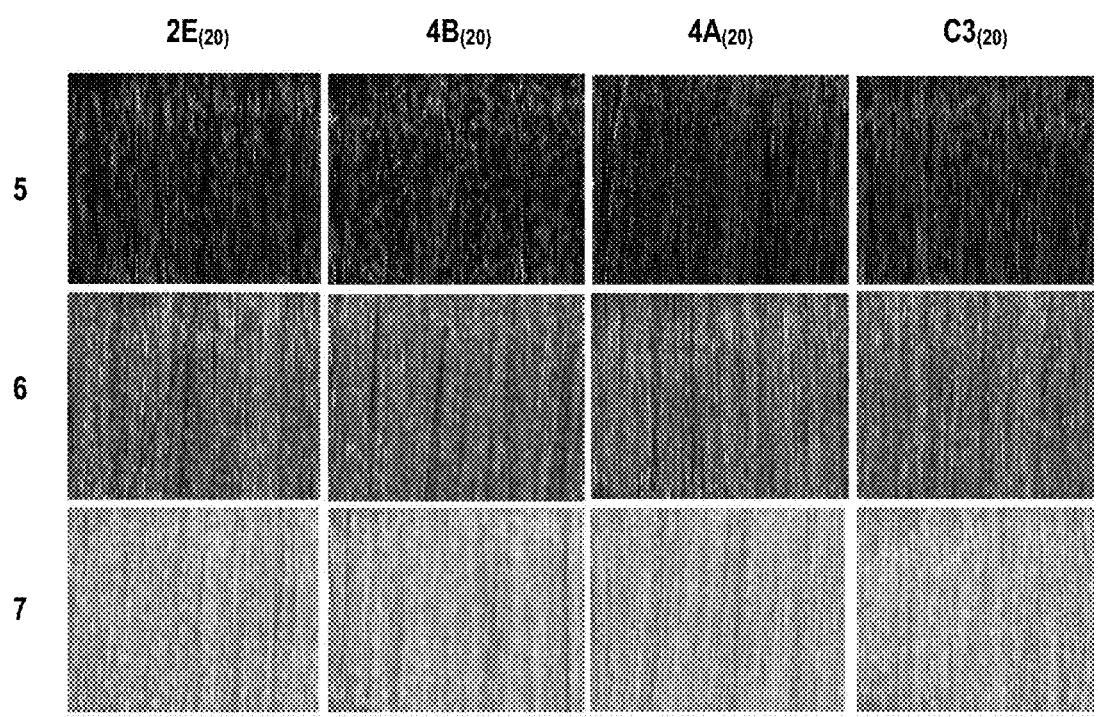
FIG. 3C shows the color of hair swatches 5-7 after treatment with mixtures in Table 8.
Figure 4A:
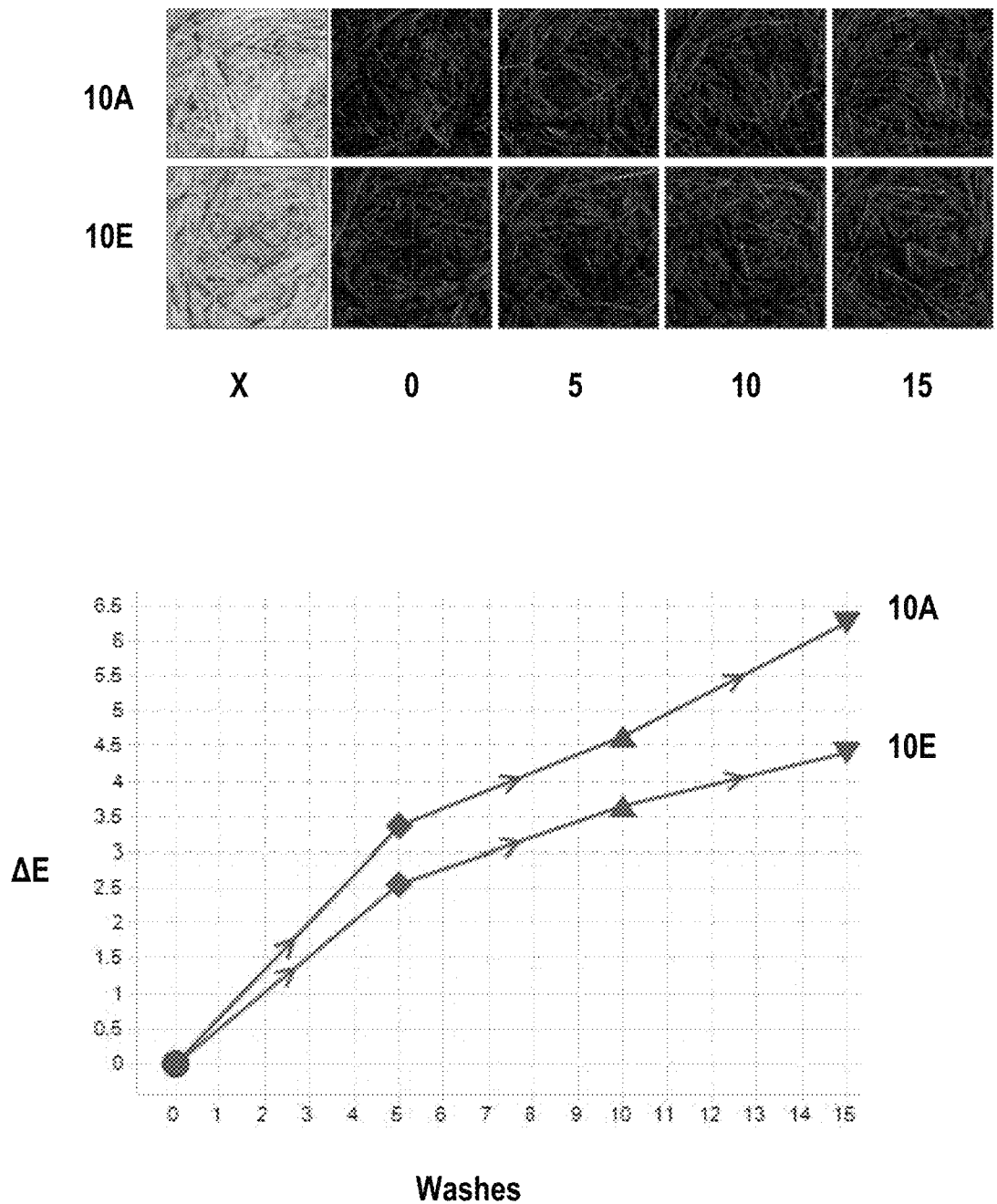
Figure 4C:
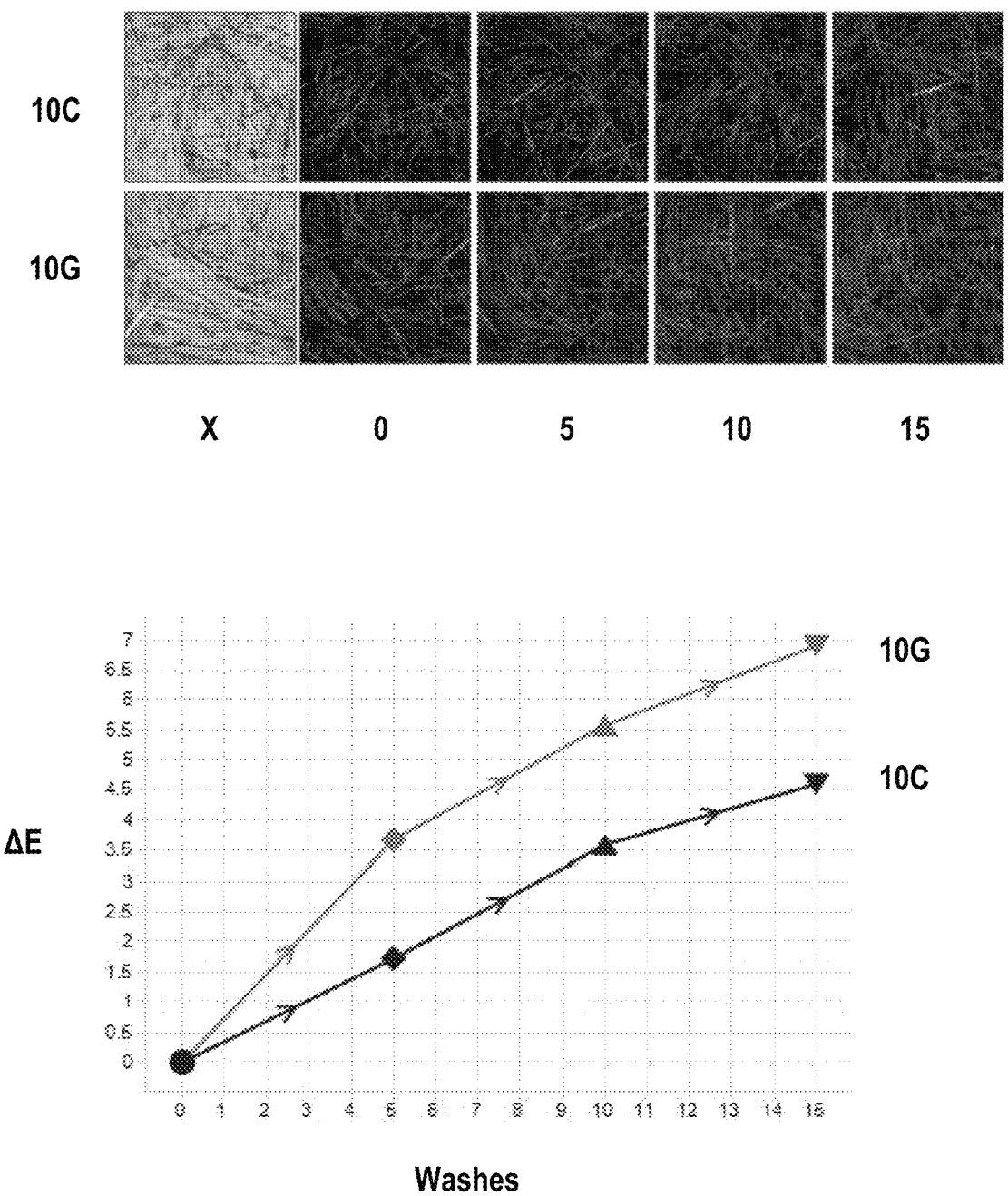
Figure 4D:
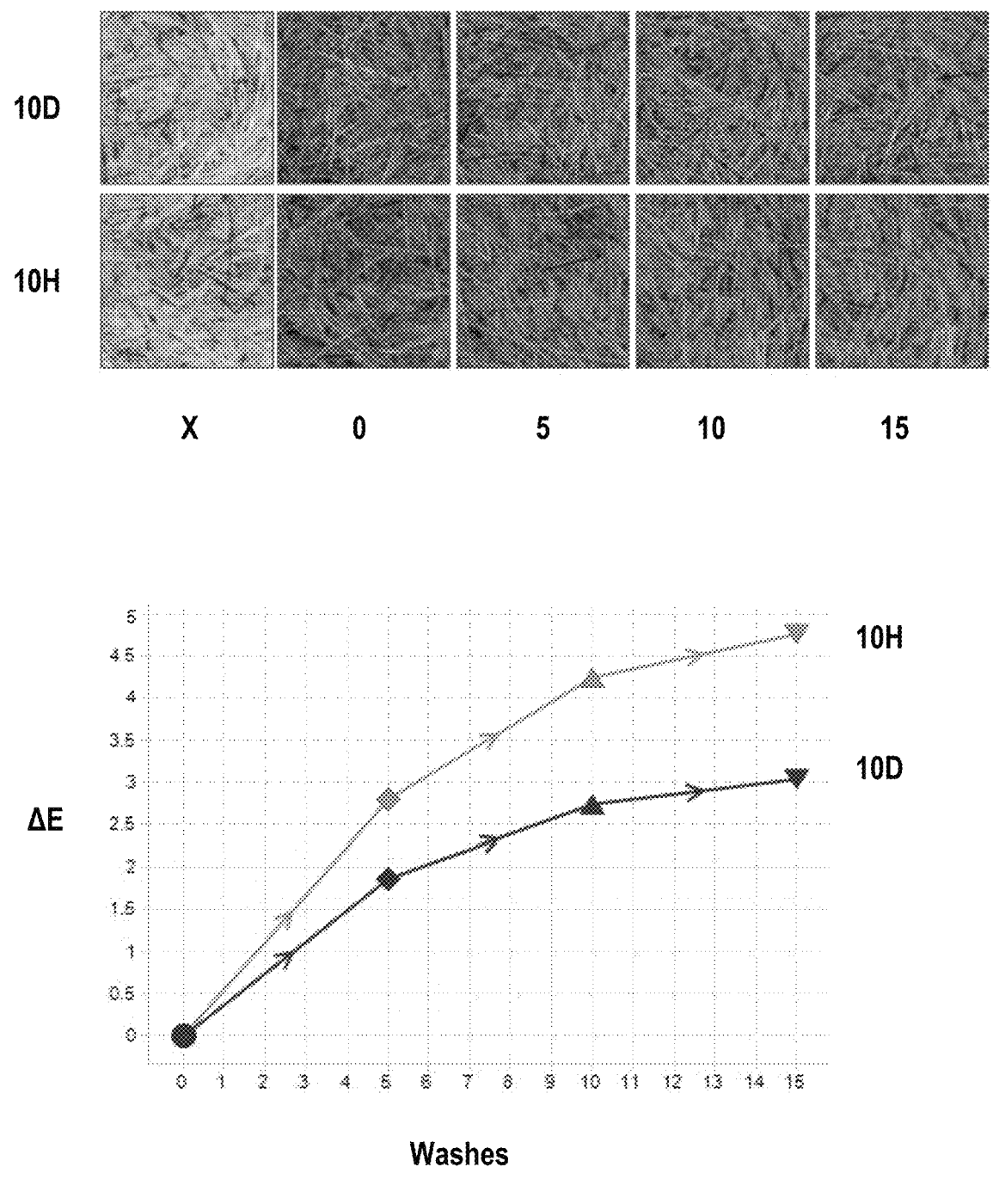

As seen in FIGS. 3A-3C, the lift obtained by each of the inventive mixtures was comparable to that of the respective comparative mixtures, despite the comparative mixtures having a large amount of mineral oil and a different solvent system than the inventive mixtures.

This example thus demonstrates that, surprisingly and unexpectedly, satisfactory lift can be achieved with hair color altering compositions according to the disclosure, comparable to lift achieved with traditional hair color altering compositions.

Example 9—Measurement of Viscosity

The viscosities of mixtures of inventive hair color bases or hair color altering compositions combined with equal amounts of 20V aqueous hydrogen peroxide oxidizing compositions were measured using a Rheomat RM 180, M3 spindle for 180 seconds under ambient conditions, as shown in Table 9:

TABLE 9

| Mixture | Hair Color Base/ Hair Color Altering Composition | Oxidizing Composition | Mixing Ratio | Mixture Viscosity (Centipoise) |
|---|---|---|---|---|
| 1H(20) | 1H | 20V | 1:1 | 1223 |
| 4J(20) | 4J | 20V | 1:1 | 1437 |
| 4K(20) | 4K | 20V | 1:1 | 1076 |
| 4L(20) | 4L | 20V | 1:1 | 1403 |

The mixtures in Table 9 have viscosities that are considered to be particularly suitable for efficient application to keratin fibers such as hair on the head, facial hair, etc., without dripping or running.

Example 10—Evaluation of Wash Resistance

The compositions in Tables 10A and 10B were prepared.

TABLE 10A

| INCI | Hair Color Altering Compositions | | | |
|---|---|---|---|---|
| | 10A | 10B | 10C | 10D |
| PEG-4 RAPESEEDAMIDE | 12.2 | 12.2 | 12.2 | 12.2 |
| ALKOXYLATED FATTY ALCOHOLS | 6.9 | 6.9 | 6.9 | 6.9 |
| OLEYL ALCOHOL | 1.1 | 1.1 | 1.1 | 1.1 |
| LAURETH-5 CARBOXYLIC ACID | 4.5 | 4.5 | 4.5 | 4.5 |
| AMMONIUM HYDROXIDE | 1.6 | 1.6 | 1.6 | 2.1 |
| ETHANOLAMINE | 4.5 | 4.5 | 4.5 | 4.5 |
| DISODIUM EDTA | 0.001 | 0.001 | 0.001 | 0.001 |
| TETRASODIUM GLUTAMATE DIACETATE | 0.24 | 0.24 | 0.24 | 0.24 |
| PERSEA GRATISSIMA (AVOCADO) OIL | 0.5 | 0.5 | 0.5 | 0.5 |
| POLOXAMER 338 | 2.0 | 2.0 | 2.0 | 2.0 |
| GLYCOLS (hexylene, propylene, and/or dipropylene glycol) | 11.5 | 11.5 | 11.5 | 11.5 |
| ETHANOL (DENATURED) | 9.5 | 9.5 | 9.5 | 9.5 |
| HAIR COLOR ALTERING AGENTS* | 1.69 | 2.49 | 1.56 | 0.37 |
| ADDITIVES (preservatives, antioxidants, fragrance, extracts) | <2 | <2 | <2 | <2 |
| WATER | QS to 100 | QS to 100 | QS to 100 | QS to 100 |

*Hair color altering compositions in Table 10A included toluene-2,5-diamine, thioglycerin, m-aminophenol, p-aminophenol, 6-hydroxyindole, hydroxyethyl-3,4-methylenedioxyaniline HCl, and/or hydroxybenzomorpholine.

TABLE 10B

| INCI | Hair Color Altering Compositions | | | |
|---|---|---|---|---|
| | 10E | 10F | 10G | 10H |
| PEG-4 RAPESEEDAMIDE | 8.1 | 8.1 | 8.1 | 8.1 |
| ALKOXYLATED FATTY ALCOHOLS | 6.9 | 6.9 | 6.9 | 6.9 |
| OLEYL ALCOHOL | 1.1 | 1.1 | 1.1 | 1.1 |
| GLYCERYL LAURYL ETHER | 7.0 | 7.0 | 7.0 | 7.0 |
| LAURETH-5 CARBOXYLIC ACID | 4.5 | 4.5 | 4.5 | 4.5 |
| AMMONIUM HYDROXIDE | 1.6 | 2.1 | 1.6 | 2.1 |
| AMMONIUM THIOLACTATE | 0.5 | 0.5 | 0.5 | 0.5 |
| ETHANOLAMINE | 4.5 | 4.5 | 4.5 | 4.5 |
| TETRASODIUM EDTA | | | | 0.002 |
| DISODIUM EDTA | 0.001 | 0.001 | 0.001 | 0.001 |
| EDTA | 0.2 | 0.2 | 0.2 | 0.2 |
| PERSEA GRATISSIMA (AVOCADO) OIL | 0.5 | 0.5 | 0.5 | 0.5 |
| POLOXAMER 338 | 2.0 | 2.0 | 2.0 | 2.0 |
| POLYQUATERNIUM-6 | | | | 1.4 |
| GLYCOLS (hexylene, propylene, and/or dipropylene glycol) | 12.2 | 12.2 | 12.2 | 12.2 |
| ETHANOL (DENATURED) | 8.2 | 8.2 | 8.2 | 8.2 |
| HAIR COLOR ALTERING AGENTS* | 1.64 | 1.71 | 0.58 | 2.1 |

TABLE 10B-continued

| | Hair Color Altering Compositions | | | |
|---|---|---|---|---|
| INCI | 10E | 10F | 10G | 10H |
| ADDITIVES (preservatives, antioxidants, fragrance, extracts) | <2 | <2 | <2 | <2 |
| WATER | QS to 100 | QS to 100 | QS to 100 | QS to 100 |

*Hair color altering compositions in Table 10B included toluene-2,5-diamine, thioglycerin, m-aminophenol, p-aminophenol, resorcinol, 2-methylresorcinol, 2,4-diaminophenoxy-ethanol HCl, 2-amino-3-hydroxypyridine, and/or N,N-bis(2-hydroxyethyl)-p-phenylene-diamine sulfate.

Each of the hair color altering compositions in Tables 10A and 10B was mixed with equal amounts (1:1 mixing ratio) of an aqueous hydrogen peroxide oxidizing composition. Equal amounts of each mixture was applied to swatches of dark blonde hair to evaluate persistence to washing, as shown in Table 10C.

TABLE 10C

| Comparison | Composition 1 | Composition 2 |
|---|---|---|
| 1 | 10A | 10E |
| 2 | 10B | 10F |
| 3 | 10C | 10G |
| 4 | 10D | 10H |

After equal leave-on times for each comparison, the swatches were rinsed, shampooed, rinsed again, and dried. Once dry, the color of each swatch was evaluated. This color is considered the starting color (0) of the treated swatches for this study.

Subsequently, each swatch was again shampooed, rinsed, dried, and the swatch color evaluated, which was repeated for a total of fifteen washes. The difference in color ($\Delta E$) of each swatch was calculated after each washing according to the following equation:

$$\Delta E = \sqrt{(L^* - L_o^*)^2 + (a^* - a_o^*)^2 + (b^* - b_o^*)^2}$$

wherein $L^*$, $a^*$, and $b^*$ represent the values measured before each washing, and $L_o^*$, $a_o^*$, and $b_o^*$ represent the values measured after each washing.

As can be seen in FIGS. 4A-4D, the color of the swatches treated with compositions 10A-10D had as good (FIGS. 4A-4B) or better (FIGS. 4C-4D) wash resistance than the color of the swatches treated with compositions 10E-10G.

The above Examples demonstrate that the hair color bases and hair color altering compositions are surprisingly able to achieve satisfactory cosmetic properties of the hair, good wash-resistance, and color deposition and coverage, shade matching, and lift comparable to traditional hair color altering compositions, with a viscosity that enables efficient application with minimal running or dripping.

It will be apparent to those skilled in the art that various modifications and variations can be made in the compositions and methods of the invention without departing from the spirit or scope of the invention.

The invention claimed is:

1. A hair color base comprising:
   (a) from about 10% to about 40% of a surfactant system comprising:
      i. at least one fatty amide,
      ii. at least one alkoxylated fatty alcohol,
      iii. at least one fatty alcohol other than the alkoxylated fatty alcohol, and
      iv. at least one anionic surfactant;
   (b) at least about 5% of at least one organic alkalizing agent;
   (c) at least one chelating agent;
   (d) optionally, at least about 0.1% of at least one natural oil; and
   (e) a solvent system comprising:
      i. from about 3% to about 25% of at least one glycol,
      ii. from about 3% to about 20% of at least one monoalcohol, and
      iii. water,
   wherein the hair color base is substantially free of mineral alkalizing agents, and
   wherein all amounts are by weight, relative to the total weight of the hair color base.

2. The hair color base of claim 1, wherein the total amount of (a)(i) fatty amides ranges from about 2% to about 15% by weight, relative to the total weight of the hair color base.

3. The hair color base of claim 1, wherein the total amount of (a)(ii) alkoxylated fatty alcohols ranges from about 3% to about 15% by weight, relative to the total weight of the hair color base.

4. The hair color base of claim 1, wherein the total amount of (a)(iii) fatty alcohols other than (a)(ii) alkoxylated fatty alcohols ranges from about 0.1% to about 5% by weight, relative to the total weight of the hair color base.

5. The hair color base of claim 1, wherein the total amount of (a)(iv) anionic surfactants ranges from about 0.5% to about 15% by weight, relative to the total weight of the hair color base.

6. The hair color base of claim 1, wherein the at least one organic alkalizing agent is chosen from monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)aminomethane, or mixtures of two or more thereof.

7. The hair color base of claim 1, wherein the total amount of (b) organic alkalizing agents ranges from about 5% to about 20% by weight, relative to the total weight of the hair color base.

8. The hair color base of claim 1, comprising at least one natural oil, wherein the total amount of natural oils ranges from about 0.1% to about 10% by weight, relative to the total weight of the hair color base.

9. The hair color base of claim 1, wherein the total amount of (e)(i) glycols ranges from about 3% to about 22% by weight, relative to the total weight of the hair color base.

10. The hair color base of claim 1, wherein the total amount of (e)(ii) monoalcohols ranges from about 4% to about 20% by weight, relative to the total weight of the hair color base.

11. A hair color altering composition comprising a hair color base of claim 1 and at least one hair color altering agent.

12. A hair color base comprising:
   (a) from about 10% to about 40% of a surfactant system comprising:
      i. at least one fatty amide,
      ii. at least one alkoxylated fatty alcohol,
      iii. at least one fatty alcohol other than the alkoxylated fatty alcohol, and
      iv. at least one anionic surfactant;

(b) an alkaline component comprising:
  i. at least about 0.5% of at least one organic alkalizing agent, and
  ii. at least one mineral alkalizing agent, present in an amount up to about 15%;
(c) at least one chelating agent;
(d) optionally, at least about 0.1% of at least one natural oil; and
(e) a solvent system comprising:
  i. from about 5% to about 30% of at least one glycol,
  ii. from about 3% to about 20% of at least one monoalcohol, chosen from $C_1$-$C_{18}$ monoalcohols, $C_1$-$C_{16}$ monoalcohols, $C_2$-$C_{12}$ monoalcohols, or $C_2$-$C_8$ monoalcohols, and
  iii. water,
wherein the hair color base is substantially free of mineral oil, and
wherein all amounts are by weight, relative to the total weight of the hair color base.

13. The hair color base of claim 12, wherein the total amount of (a)(i) fatty amides ranges from about 5% to about 25% by weight, relative to the total weight of the hair color base.

14. The hair color base of claim 12, wherein the total amount of (a)(ii) alkoxylated fatty alcohols ranges from about 3% to about 20% by weight, relative to the total weight of the hair color base.

15. The hair color base of claim 12, wherein the total amount of (a)(iii) fatty alcohols other than (a)(ii) alkoxylated fatty alcohol ranges from about 0.1 to about 6% by weight, relative to the total weight of the hair color base.

16. The hair color base of claim 12, wherein the total amount of (a)(iv) anionic surfactants ranges from about 0.5% to about 15% by weight, relative to the total weight of the hair color base.

17. The hair color base of claim 12, wherein the at least one organic alkalizing agent is chosen from monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures of two or more thereof.

18. The hair color base of claim 12, wherein the total amount of (b)(i) organic alkalizing agents ranges from about 0.5% to about 10% by weight, relative to the total weight of the hair color base.

19. The hair color base of claim 12, wherein the at least one mineral alkalizing agent is chosen from ammonia, ammonium carbonates, sodium carbonates, potassium carbonates, ammonium bicarbonates, sodium bicarbonates, potassium bicarbonates, ammonium hydroxides, sodium hydroxides, potassium hydroxides, or mixtures of two or more thereof.

20. The hair color base of claim 12, wherein the total amount of (b)(ii) mineral alkalizing agents ranges from about 0.01% to about 10% by weight, relative to the total weight of the hair color base.

21. The hair color base of claim 12 comprising at least one natural oil, wherein the total amount of natural oils ranges from about 0.1% to about 10% by weight, relative to the total weight of the hair color base.

22. The hair color base of claim 12, wherein the total amount of (e)(i) glycols ranges from about 6% to about 28% by weight, relative to the total weight of the hair color base.

23. The hair color base of claim 12, wherein the total amount of (e)(ii) monoalcohols ranges from about 4% to about 18% by weight, relative to the total weight of the hair color base.

24. A hair color altering composition comprising a hair color base of claim 12 and at least one hair color altering agent.

* * * * *